United States Patent
Reinehr et al.

(10) Patent No.: US 7,476,699 B2
(45) Date of Patent: Jan. 13, 2009

(54) AMINO- AND HYDROXYSUBSTITUTED TRIPHENYL-S-TRIAZINES AS STABILIZERS

(75) Inventors: Dieter Reinehr, Kandern (DE); Georges Metzger, Moernach (FR); Peter Michaelis, Geispitzen (FR); Helmut Luther, Grenzach-Wyhlen (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 11/891,554

(22) Filed: Aug. 10, 2007

(65) Prior Publication Data

US 2007/0274933 A1 Nov. 29, 2007

Related U.S. Application Data

(63) Continuation of application No. 10/013,885, filed on Dec. 11, 2001, now abandoned, which is a continuation of application No. 09/651,615, filed on Aug. 30, 2000, now abandoned, which is a continuation of application No. 09/155,560, filed as application No. PCT/EP97/01331 on Sep. 30, 1998, now abandoned.

(30) Foreign Application Priority Data

Apr. 2, 1996 (GB) ................. 9606970.3

(51) Int. Cl.
C08K 5/3492 (2006.01)
(52) U.S. Cl. ............... 524/100; 8/190; 424/59; 424/60; 424/70.9; 514/972; 544/92; 544/215; 564/411
(58) Field of Classification Search ........... 424/59, 424/60, 70.9; 8/490; 514/972; 524/100; 544/92, 215; 564/411
See application file for complete search history.

(56) References Cited

U.S. PATENT DOCUMENTS

| | | | | |
|---|---|---|---|---|
| 3,118,887 | A | * | 1/1964 | Pinto et al. ............... 544/216 |
| 3,259,627 | A | * | 7/1966 | Duennenberger et al. ... 544/216 |
| 3,270,016 | A | * | 8/1966 | Duennenberger et al. ... 544/211 |
| 3,278,534 | A | * | 10/1966 | Schellenbaum et al. ..... 415/141 |
| 3,293,249 | A | * | 12/1966 | Biland et al. .............. 544/219 |
| 3,544,566 | A | | 12/1970 | Brunetti .................... 544/92 |
| 3,896,125 | A | | 7/1975 | Helmo et al. ............ 260/249.5 |
| 3,957,780 | A | * | 5/1976 | Grossmann ................ 544/211 |
| 4,619,956 | A | * | 10/1986 | Susi ........................ 524/87 |
| 4,990,671 | A | | 2/1991 | Dunski .................... 564/411 |
| 5,461,151 | A | | 10/1995 | Waterman ................. 544/216 |
| 5,959,008 | A | | 9/1999 | Birbaum et al. ........... 524/100 |
| 6,013,704 | A | | 1/2000 | Hayoz et al. ............. 524/100 |
| 6,040,443 | A | | 3/2000 | Metzger et al. ............ 544/92 |

FOREIGN PATENT DOCUMENTS

| | | |
|---|---|---|
| EP | 0200190 | 11/1986 |
| GB | 1152980 | 5/1969 |
| GB | 1155506 | 6/1969 |
| WO | 96/28431 | 9/1996 |

OTHER PUBLICATIONS

Chem. Abstr. vol. 81, No. 18, 107222y for JP 48038338 (1973).

(Continued)

Primary Examiner—Peter Szekely
(74) Attorney, Agent, or Firm—Mervin G. Wood

(57) ABSTRACT

The present invention provides compounds having the formula:

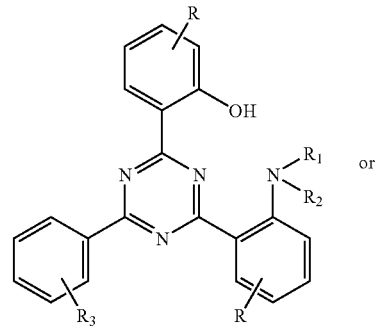

(1)

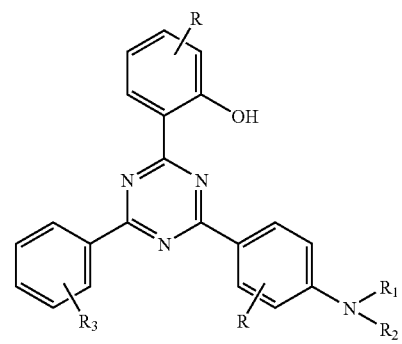

(1A)

in which R is hydrogen, hydroxy, halogen, $C_1$-$C_{20}$-alkyl, $C_4$-$C_{12}$cycloalkyl, $C_2$-$C_{20}$alkenyl, $C_2$-$C_{20}$alkynyl, $C_1$-$C_{20}$-alkoxy, $C_4$-$C_{12}$cycloalkoxy, $C_2$-$C_{20}$alkenoxy, $C_2$-$C_{20}$alkynoxy or $C_7$-$C_{13}$aralkyl; $R_1$ and $R_2$, independently, are hydrogen, $C_1$-$C_{20}$alkyl, $C_4$-$C_{12}$cycloalkyl, $C_7$-$C_{13}$ aralkyl, —C(═O)—$R_4$ (in which $R_4$ is $C_1$-$C_{20}$alkyl, $C_2$-$C_{20}$alkyl interrupted by 1 to 6 oxygen atoms, hetero-substituted $C_1$-$C_{20}$alkyl, $C_4$-$C_{12}$cycloalkyl, $C_2$-$C_{20}$alkenyl, $C_2$-$C_{20}$alkynyl, $C_1$-$C_{20}$-alkoxy, $C_4$-$C_{12}$cycloalkoxy, $C_2$-$C_{20}$alkenoxy, $C_2$-$C_{20}$alkynoxy, $C_6$-$C_{12}$ aryl, $C_6$-$C_{12}$ aryloxy or $C_7$-$C_{13}$ aralkyl), or —C(═O)—NH—$R_1$ in which $R_1$ has its previous significance; and $R_3$ is hydrogen, halogen, hydroxy, $C_1$-$C_{20}$alkyl, $C_4$-$C_{12}$cycloalkyl, $C_2$-$C_{20}$alkenyl, $C_2$-$C_{20}$alkynyl, $C_1$-$C_{20}$-alkoxy, $C_4$-$C_{12}$cycloalkoxy, $C_2$-$C_{20}$alkenoxy, $C_2$-$C_{20}$alkynoxy, phenyl, $C_7$-$C_{13}$ aralkyl or —N($R_1$)($R_2$) in which $R_1$ and $R_2$ have their previous significance, or $R_1$ and $R_2$ together form a $C_4$-$C_{12}$ membered ring.

The new triphenyltriazine compounds have improved absorption spectrum characteristics and superior resistance to exposure to UV light, relative to known triphenyltriazine compounds.

11 Claims, No Drawings

OTHER PUBLICATIONS

Derwent Abstr. 96-000588/01 for DE 4444258 (1995).
Derwent Abstr. 94-027064/04 for DE 4223065 (1994).
Ryabukhin et al., Khim. Geterotsikl. Soedin., No. 4, (1992), pp. 540-549, XP 002034496, "Synthesis and Structure of o-Hydroxyaryl-1,2,4-Oxadiazoles".
Dorofeenko et al., Chem. Heterocycl. Comp., (1976), pp. 621-623, XP 000654710, "Acylation of Salicylnitrile and Salicylaldoxime as a Method for the Synthesis of 4H-1,3-benzoxazin-4-onium salts".
Stegmann et al., Chem. Ber., vol. 118, N. 11, (1985), pp. 4632-4636, XP 000654619, "Synthese von 2-Methyl-4H-1,3-Benzoxazin-4-onen und Analogen Verbindungen".
Kollenz et al., Monatsh. Chem., vol. 99, No. 6, (1968), pp. 2167-2170, XP 000654620.
Catarzi et al., J. Med. Chem., vol. 38, No. 12, (1995), pp. 2196-2201, XP 000652274.

* cited by examiner

AMINO- AND HYDROXYSUBSTITUTED TRIPHENYL-S-TRIAZINES AS STABILIZERS

This application is a continuation of application Ser. No. 10/013,885, filed Dec. 11, 2001, now abandoned, which is a continuation of application Ser. No. 09/651,615, filed Aug. 30, 2000, now abandoned, which is a continuation of application Ser. No. 09/155,560, filed Sep. 30, 1998, now abandoned, which is the National Stage of International Application PCT/EP97/01331, filed Mar. 17, 1997, herein incorporated by reference.

The present invention relates to new compounds and, in particular, to new amino- or amido-substituted triazine compounds having excellent absorption spectrum characteristics and good resistance to exposure to UV light, and to the use of the new compounds as UV absorbers.

If it is desired to increase the light stability of an organic material, especially a coating, a light stabilizer is usually added. A class of light stabilizers which is very frequently employed comprises the UV absorbers, which protect the material by absorbing the harmful radiation via chromophores. An important group of UV absorbers is the triphenyltriazines, which are described, e.g., in EP-A-434 608, EP-A-520 938, U.S. Pat. No. 4,619,956, EP-A-483 488, EP-A-500 496, EP-A-502 816 and EP-A-506 615.

A new group of triphenyltriazine compounds has now been found which have improved absorption spectrum characteristics and superior resistance to exposure to UV light, relative to known triphenyltriazine compounds.

According to the present invention, there are provided compounds having the formula:

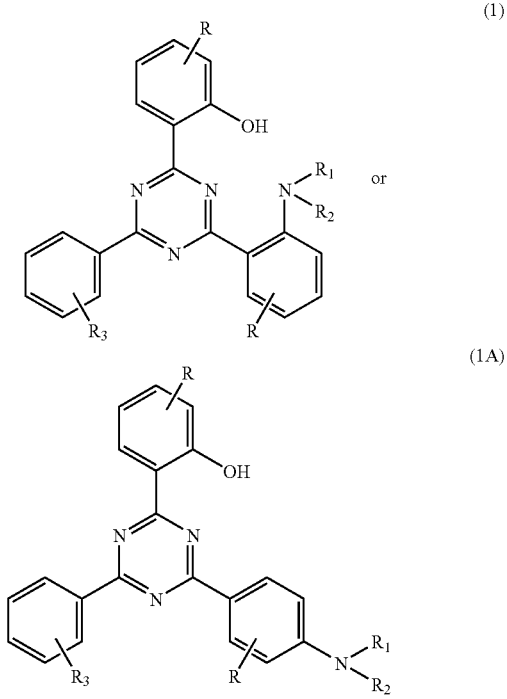

in which R is hydrogen, hydroxy, halogen, $C_1$-$C_{20}$-alkyl, $C_4$-$C_{12}$cycloalkyl, $C_2$-$C_{20}$alkenyl, $C_2$-$C_{20}$alkynyl, $C_1$-$C_{20}$-alkoxy, $C_4$-$C_{12}$cycloalkoxy, $C_2$-$C_{20}$alkenoxy, $C_2$-$C_{20}$alkynoxy or $C_7$-$C_{13}$aralkyl, preferably hydrogen, hydroxy, halogen, $C_1$-$C_{20}$-alkyl or $C_1$-$C_{20}$-alkoxy; $R_1$ and $R_2$, independently, are hydrogen, $C_1$-$C_{20}$alkyl, $C_4$-$C_{12}$cycloalkyl, $C_7$-$C_{13}$ aralkyl, —C(=O)—$R_4$ (in which $R_4$ is $C_1$-$C_{20}$alkyl, $C_2$-$C_{20}$alkyl interrupted by 1 to 6 oxygen atoms, hetero-substituted $C_1$-$C_{20}$alkyl, $C_4$-$C_{12}$cycloalkyl, $C_2$-$C_{20}$alkenyl, $C_2$-$C_{20}$alkynyl, $C_1$-$C_{20}$-alkoxy, $C_4$-$C_{12}$cycloalkoxy, $C_2$-$C_{20}$alkenoxy, $C_2$-$C_{20}$alkynoxy, $C_6$-$C_{12}$ aryl, $C_6$-$C_{12}$ aryloxy or $C_7$-$C_{13}$ aralkyl), or —C(=O)—NH—$R_1$ in which $R_1$ has its previous significance, preferably $R_1$ and $R_2$, independently, are hydrogen, $C_1$-$C_{20}$alkyl, $C_7$-$C_{13}$ aralkyl, —C(=O)—$R_4$ (in which $R_4$ is $C_1$-$C_{20}$alkyl, $C_2$-$C_{20}$alkyl interrupted by 1 to 6 oxygen atoms, $C_2$-$C_{20}$alkenyl, $C_6$-$C_{12}$ aryl or $C_6$-$C_{12}$ aryloxy), or —C(=O)—NH—$R_1$ in which $R_1$ has its previous significance; and $R_3$ is hydrogen, halogen, hydroxy, $C_1$-$C_{20}$alkyl, $C_4$-$C_{12}$cycloalkyl, $C_2$-$C_{20}$alkenyl, $C_2$-$C_{20}$alkynyl, $C_1$-$C_{20}$-alkoxy, $C_4$-$C_{12}$cycloalkoxy, $C_2$-$C_{20}$alkenoxy, $C_2$-$C_{20}$alkynoxy, phenyl, $C_7$-$C_{13}$ aralkyl or —N($R_1$)($R_2$) in which $R_1$ and $R_2$ have their previous significance, or $R_1$ and $R_2$ together form a $C_4$-$C_{12}$ membered ring, preferably $R_3$ is hydrogen, halogen, hydroxy, $C_1$-$C_{20}$alkyl, phenyl, —N($R_1$)($R_2$) in which $R_1$ and $R_2$ have their previous significance or $R_1$ and $R_2$ together form a $C_4$-$C_{12}$ membered ring.

When R and/or $R_3$ is halogen, such halogen substituents are fluorine, bromine, iodine or, especially, chlorine substituents.

$C_1$-$C_{20}$alkyl groups R, $R_1$, $R_2$, $R_3$ and/or $R_4$ may be branched or unbranched such as methyl, ethyl, n-propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, n-nonyl, n-decyl, n-undecyl, 1-methylundecyl, n-dodecyl, 1,1,3,3,5,5-hexamethylhexyl, n-tridecyl, n-tetradecyl, n-pentadecyl, n-hexadecyl, n-heptadecyl, n-octadecyl and n-eicosyl.

$C_1$-$C_{20}$alkoxy groups R, $R_3$ and $R_4$ may be branched or unbranched such as methoxy, ethoxy, n-propoxy, isopropoxy, n-butoxy, sec-butoxy, isobutoxy, t-butoxy, 2-ethylbutoxy, n-pentoxy, isopentoxy, 1-methylpentoxy, 1,3-dimethylbutoxy, n-hexoxy, 1-methylhexoxy, n-heptoxy, isoheptoxy, 1,1,3,3-tetramethylbutoxy, 1-methylheptoxy, 3-methylheptoxy, n-octoxy, 2-ethylhexoxy, 1,1,3-trimethylhexoxy, 1,1,3,3-tetramethylpentoxy, n-nonoxy, n-decoxy, n-undecoxy, 1-methylundecoxy, n-dodecoxy, 1,1,3,3,5,5-hexamethylhexoxy, n-tridecoxy, n-tetradecoxy, n-pentadecoxy, n-hexadecoxy, n-heptadecoxy, n-octadecoxy and n-eicosoxy, preferably methoxy, ethoxy or propoxy groups, especially methoxy groups.

When $R_4$ is $C_2$-$C_{20}$alkyl which is interrupted by from 1 to 6 oxygen atoms, this group may be branched or unbranched such as 3-oxabutyl, 3-oxapentyl, 3-oxahexyl, 3-oxaoctyl, 3-oxadecyl, 3-oxadodecyl, 3-oxatetradecyl, 3-oxahexadecyl, 3-oxaoctadecyl, 3,6-dioxaheptyl, 3,6-dioxaoctyl, 3,6-dioxadecyl, 3,6-dioxadodecyl, 3,6-dioxatetradecyl, 3,6-dioxaheptadecyl, 3,6,9-trioxadecyl, 3,6,9-trioxaundecyl, 3,6,9-trioxadodecyl, 3,6,9-trioxatetradecyl, 3,6,9-trioxahexadecyl or 3,6,9-trioxadecaheptyl.

When $R_4$ is $C_1$-$C_{20}$alkyl which is substituted by a heterocyclic residue, it may be any of the $C_1$-$C_{20}$alkyl groups listed above in relation to $C_1$-$C_{20}$alkyl groups $R_1$, $R_2$, $R_3$ and/or $R_4$, preferably methyl, ethyl or propyl groups, especially a methyl group, substituted by a morpholinyl, piperidyl, 2,2,6,6-tetramethylpiperidyl, piperazinyl or N-methylpiperazinyl residue.

When $R_4$ is a $C_2$-$C_{20}$alkenyl group, it may be, e.g., allyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

When $R_4$ is a $C_6$-$C_{10}$aryl group, it is a naphthyl or, preferably, a phenyl group.

$C_7$-$C_{20}$aralkyl groups $R_2$ and/or $R_4$ may be naphthylalkyl groups but are preferably phenylalkyl groups. Examples of $C_7$-$C_{20}$ phenylalkyl groups $R_2$ and/or $R_4$ include benzyl, α-methylbenzyl, α,α-dimethylbenzyl, phenylethyl, phenylpropyl, phenyl-butyl, phenylpentyl, phenylhexyl, phenylheptyl, phenyloctyl, phenylnonyl, phenyldecyl, phenyldodecyl and phenyltetradecyl.

$C_6$-$C_{10}$aryl groups $R_4$ and $C_7$-$C_{20}$aralkyl groups $R_2$ and/or $R_4$ may be unsubstituted or may be substituted by one of more substituents. Examples of such substituent groups include hydroxyl, —$NH_2$, —$NHR_1$, —$NR_1R_2$ (in which $R_1$ and $R_2$ have their previous significance), halogen, $C_1$-$C_{20}$alkyl, $C_1$-$C_{20}$alkoxy, $C_2$-$C_{20}$alkenyl, $C_3$-$C_{20}$alkynyl, $C_6$-$C_{12}$aryl, sulfonyl, carboxyl, (meth)acryloxy or (meth)acrylamino.

Preferred compounds according to the invention are those having the formula:

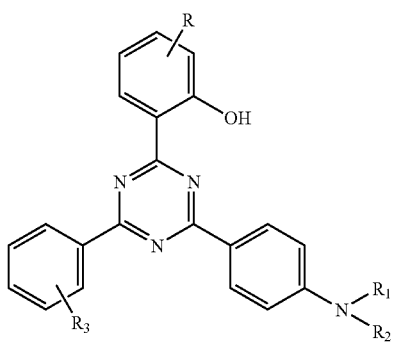

(2)

in which R is hydrogen or $C_1$-$C_4$alkoxy, preferably methoxy; either $R_1$ and $R_2$ are each hydrogen, or $R_1$ is hydrogen and $R_2$ is —C(=O)—$R_4$ in which $R_4$ is $C_1$-$C_{20}$alkyl, $C_2$-$C_{20}$alkenyl, $C_1$-$C_{20}$alkoxy, phenyl optionally substituted with $C_1$-$C_4$alkoxy or $CH_2$—$(OCH_2CH_2)_n$—$OCH_3$ in which n is an integer from 1 to 5; and $R_3$ is hydrogen, $C_1$-$C_{20}$alkyl, $C_1$-$C_4$alkoxy or hydroxy; and in which preferably R is hydrogen or methoxy; either $R_1$ and $R_2$ are each hydrogen, or $R_1$ is hydrogen and $R_2$ is —CO—$CH_2$—$(OCH_2CH_2)_n$—$OCH_3$ in which n is an integer from 1 to 5; and $R_3$ is hydrogen, $C_1$-$C_{20}$alkyl, $C_2$-$C_{20}$alkenyl, hydroxy, methoxy, phenyl or methoxy-substituted phenyl.

Particularly preferred compounds according to the invention are those having the formula:

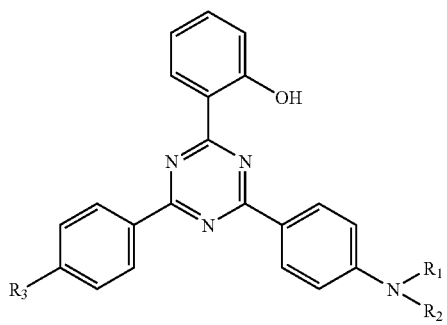

(3)

in which either $R_1$ and $R_2$ are each hydrogen, or $R_1$ is hydrogen and $R_2$ is —C(=O)—$R_4$ in which $R_4$ is $C_1$-$C_{20}$alkyl, $C_2$-$C_{20}$alkenyl, $C_1$-$C_{20}$alkoxy, phenyl optionally substituted with $C_1$-$C_4$alkoxy or $CH_2$—$(OCH_2CH_2)_n$—$OCH_3$ in which n is an integer from 1 to 5; and $R_3$ is hydrogen, hydroxy, $C_1$-$C_{20}$alkyl, methoxy or phenyl; and in which preferably either $R_1$ and $R_2$ are each hydrogen, or $R_1$ is hydrogen and $R_2$ is —CO—$CH_3$; and $R_3$ is hydrogen, methoxy or phenyl.

The new compounds of formula (1) or (1A) may be prepared by any of several synthetic routes.

For example, an o-hydroxybenzamide of formula:

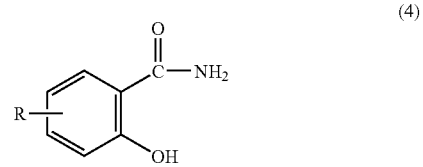

(4)

in which R has its previous significance, may be reacted with a benzoyl chloride of formula:

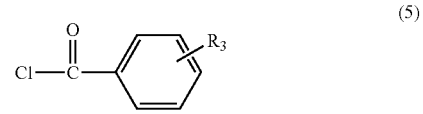

(5)

in which $R_3$ has its previous significance, to produce a compound of formula:

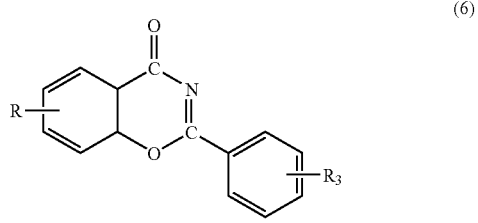

(6)

in which R and $R_3$ have their previous significance; and the compound of formula (6) is then reacted with a benzamidine having the formula:

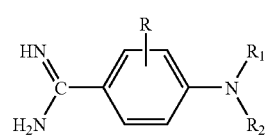

(7)

in which R, $R_1$ and $R_2$ have their previous significance, to produce a compound of formula (1A).

In a second synthetic route, an o-hydroxybenzamide of formula (4) may be reacted with a p-nitro-benzoyl chloride of formula:

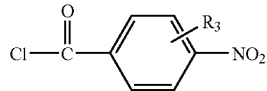 (8)

in which $R_3$ has its previous significance, to produce a compound having the formula:

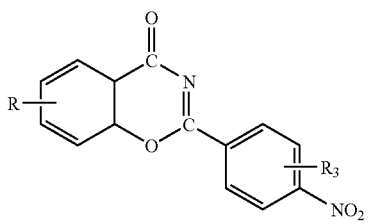 (9)

in which R and $R_3$ have their previous significance, then reacting the compound of formula (9) with a benzamidine having the formula:

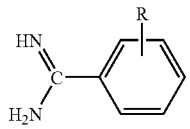 (10)

in which R has its previous significance, to produce a compound of formula:

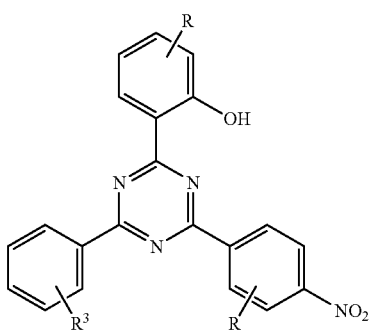 (11)

in which R and $R_3$ have their previous significance, and finally hydrogenating the compound of formula (11) to produce a compound of formula (1A).

In a third synthetic method, for the production of specific compounds of formula (1) or (1A), an o-hydroxybenzamide of formula (4) may be reacted with a p-acylaminobenzoyl chloride having the formula:

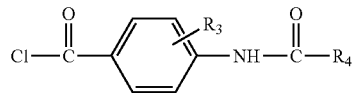 (12)

in which $R_3$ and $R_4$ have their previous significance, to produce compounds having the formula:

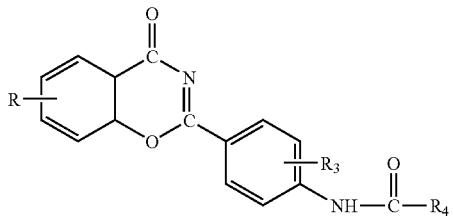 (13)

in which R, $R_3$ and $R_4$ have their previous significance, and finally reacting the compound of formula (13) with a compound of formula (10) to produce a compound of formula:

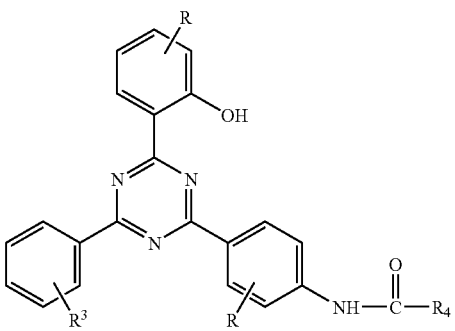 (14)

in which R, $R_3$ and $R_4$ have their previous significance.

The novel triazine compounds are very good UV absorbers and are therefore useful as stabilizers for organic polymers, especially coating materials, against damage thereto by light and as light stabilizers for textile fibre materials.

Particular advantages of the novel compounds include their surprisingly high absorption in the 300 to 400 nm region of the electromagnetic spectrum. Material stabilized with the compounds according to the invention features outstanding resistance to the effects of weathering and light, and outstanding photostability of the incorporated stabilizer.

The materials to be stabilized can be, for example, oils, fats, waxes, cosmetics or biocides. A particularly interesting application is in polymeric materials which are present in plastics, rubbers, paints and other coating materials, photographic material or adhesives. Examples of polymers and other substrates which can be stabilized in this way are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for example of cyclopentene or norbornene; furthermore polyethylene (which optionally can be crosslinked), for example high density polyethylene (HDPE), polyethylene of high density and high molecular mass (HDPE-HMW), polyethylene of high density and ultra-high molecular mass (HDPE-UHMW), medium density polyethylene (MDPE), low density polyethylene (LDPE), linear low density polyethylene (LLDPE), branched low density polyethylene (BLDPE).

Polyolefins, i.e. polymers of monoolefins exemplified in the preceding paragraph, in particular polyethylene and polypropylene, can be prepared by different, and especially by the following, methods:

a) radical polymerization (normally under high pressure and at elevated temperature); or b) catalytic polymerization using a catalyst that normally contains one or more metals of group IVb, Vb, VIb or VIII of the Periodic Table. These metals usually have one or more ligands, such as oxides, halides, alcoholates, esters, ethers, amines, alkyls, alkenyls and/or aryls that may be either π- or σ-coordinated. These metal complexes may be in the free form or fixed on substrates, for example on activated magnesium chloride, titanium (III) chloride, alumina or silicon oxide. These catalysts may be soluble or insoluble in the polymerization medium. The catalysts can be activated by themselves in the polymerization or further activators may be used, for example metal alkyls, metal hydrides, metal alkyl halides, metal alkyl oxides or metal alkyloxanes, the metals being elements of groups Ia, IIa and/or IIIa of the Periodic Table. The activators may be modified, for example, with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned under 1), for example polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers and alternating or random polyalkylene/carbon monoxide copolymers and mixtures thereof with other polymers, for example polyamides.

4. Hydrocarbon resins (for example $C_5$-$C_8$) including hydrogenated modifications thereof (e.g. tackifiers) and mixtures of polyalkylenes and starch.

5. Polystyrene poly-(p-methylstyrene), poly-(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, as well as mixtures thereof with the copolymers mentioned under 6), for example the copolymer mixtures known as ABS, MBS, ASA or AES polymers.

8. Halogen-containing polymers such as polychloroprene, chlorinated rubber, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride; polyvinylidene fluoride; as well as copolymers thereof such as vinyl chloride/vinylidene chloride, vinyl chloride/vinyl acetate or vinylidene chloride/vinyl acetate.

9. Polymers derived from α,β-unsaturated acids and derivatives thereof such as polyacrylates and polymethacrylates, polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers derived from unsaturated alcohols and amines of the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in point 1.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain comonomers, for example ethylene oxide; polyacetals modified with thermoplastic polyurethanes, acrylates or MBS.

14. Polyphenylene oxides and sulfides, and mixtures thereof with styrene polymers or polyamides.

15. Polyurethanes derived from hydroxyl-terminated polyethers, polyesters and polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides starting from m-xylene, diamine and adipic acid; polyamides prepared from hexamethylenediamine and isophthalic and/or terephthalic acid and with or without an elastomer as modifier, for example poly-2,4,4-trimethylhexamethylene terephthalamide or poly-m-phenylene isophthalamide. Block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol. As well as polyamides or copolyamides modified with EPDM or ABS; and polyamides condensed during processing (RIM polyamide systems).
17. Polyureas, polyimides, polyamide-imides, polyetherimides, polyesterimides, polyhydantoins and polybenzimidazoles.
18. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalates and polyhydroxybenzoates, as well as block polyether esters derived from hydroxyl-terminated polyethers; and also polyesters modified with polycarbonates or MBS; and acid-modified polyesters.
19. Polycarbonates and polyester carbonates.
20. Polysulfones, polyether sulfones and polyether ketones.
21. Crosslinked polymers derived from aldehydes on the one hand and phenols, urea or melamine on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example from epoxy acrylates, urethane acrylates or polyester acrylates.
25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, for example products of bisphenol A diglycidyl ethers, bisphenol F diglycidyl ethers, which are crosslinked by means of customary hardeners, for example anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and derivatives.
28. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention therefore also relates to a composition comprising (A) an organic material which is sensitive to damage by light, oxygen and/or heat, and (B) as stabilizer, a compound of the formula (1) or (1A).

The invention also relates to a process for stabilizing organic material against damage by light, oxygen and/or heat, which comprises adding thereto, as stabilizer, a compound of the formula (1) or (1A), and to the use of the compound of the formula (1) or (1A) for stabilizing organic material.

The amount of the stabilizer to be used depends on the organic material to be stabilized and on the intended use of the stabilized material. In general, the novel composition comprises from 0.01 to 15 parts by weight, in particular from 0.05 to 10 parts by weight, especially from 0.1 to 5 parts by weight, of the stabilizer (component B) per 100 parts by weight of component (A).

The stabilizer (component (B)) can also be a mixture of two or more compounds of the formula (1) or (1A). In addition to the novel compounds, the novel compositions can also comprise other stabilizers or other additives, for example antioxidants, further light stabilizers, metal deactivators, phosphites or phosphonites. Examples of these stabilizers are the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl) phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2, 2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2, 2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3, 5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylol-propane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono-und dialkylated tert-butyldiphenylamines, 2,3-dihydro-3,3-dimethyl-4H-1,4-benzothiazine, phenothiazine, a mixture of mono-und dialkylated tert-butyl/tert-octylphenothiazines, a mixture of mono-und dialkylated tert-octylphenothiazines, N-allylphenothiazin, N,N,N',N'-tetraphenyl-1,4-diaminobut-2-ene, N,N-bis-(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-β-methoxy-cinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4,5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4,5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro[4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, and/or a 2,4-bis(4-phenylphenyl)-6-aryl-triazine e.g. of WO 96/28431, such as 2-[4-(dodecyloxy/tridecyloxy-2-hydroxypropoxy)-2-hydroxyphenyl]-4,6-bis(4-phenylphenyl)-1,3,5-triazine, 2-(2-hydroxy-4-octyloxyphenyl)-4,6-bis(4-phenylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl))pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 2,2',2''-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite.

Especially preferred are the following phosphites:

Tris(2,4-di-tert-butylphenyl)phosphite (Irgafos® 168, Ciba-Geigy), tris(nonylphenyl)phosphite, (A)
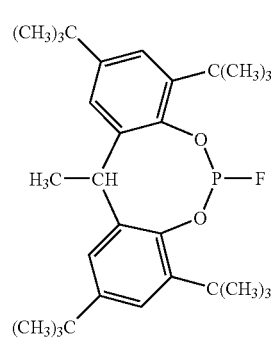

(B)
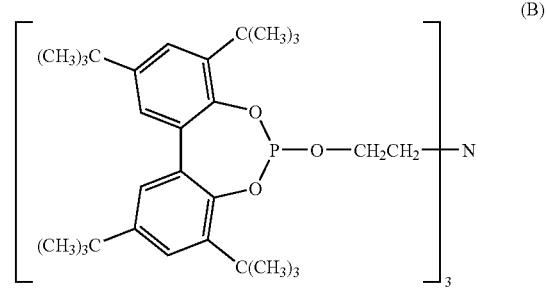

(C)
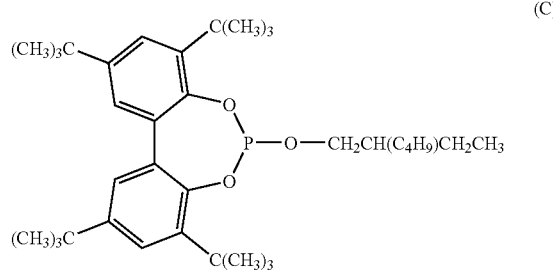

(D)
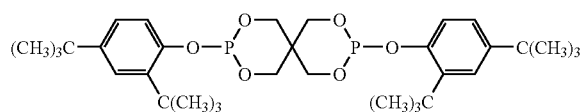

(E)
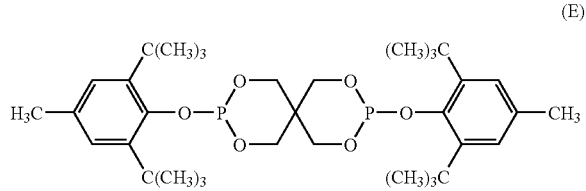

(F)
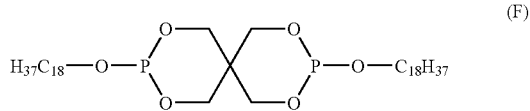

-continued

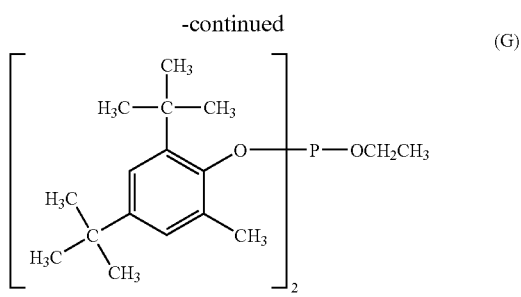

(G)

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The type and amount of the further stabilizers added is determined by the type of substrate to be stabilized and on its intended use; frequently, from 0.1 to 5% by weight, based on the polymer to be stabilized, are used.

The novel stabilizers can with particular advantage be employed in compositions in which component (A) is a synthetic organic polymer, especially a thermoplastic polymer, a binder for coatings, for example paints, or a photographic material. Examples of suitable thermoplastic polymers are polyolefins and polymers comprising heteroatoms in the main chain. Preference is also given to compositions in which component (A) is a thermoplastic polymer comprising nitrogen, oxygen and/or sulphur, especially nitrogen or oxygen, in the main chain.

Also of interest are compositions in which component (A) is a polyolefin, for example polyethylene or polypropylene.

Incorporation into the organic polymers, for example into the synthetic organic and, in particular, thermoplastic polymers, can be carried out by addition of the novel triphenyl-substituted triazine compound and any further additives by the methods conventional in the art. The incorporation can expediently be made before or during shaping, for example by mixing the pulverulent components or by adding the stabilizer to the melt or solution of the polymer, or by applying the dissolved or dispersed compounds to the polymer, with or without subsequent evaporation of the solvent. Elastomers can also be stabilized as latices. Another way of incorporating the novel mixtures into polymers comprises adding them before or during polymerization of the corresponding monomers or before crosslinking.

The novel compounds can also be added to the plastics to be stabilized in the form of a master batch which comprises these compounds, for example, in a concentration of from 2.5 to 25% by weight.

The novel compounds can expediently be incorporated by the following methods:

as an emulsion or dispersion (for example to latices or emulsion polymers)

as a dry mix during mixing of additional components or polymer mixtures by direct addition to the processing equipment (for example extruders, internal mixers, etc.)

as a solution or melt.

The stabilized polymer compositions obtained in this way can be converted into shaped articles, for example fibres, films, tapes, sheets, sandwich boards, containers, pipes and other profiles, by conventional methods, for example hot pressing, spinning, extrusion or injection moulding.

The invention therefore additionally relates to the use of the polymer composition according to the invention for the production of a shaped article.

Use in multilayer systems is also of interest. In this case, a novel polymer composition having a relatively high content of novel stabilizer, for example, 5-15% by weight, is applied in a thin film (10-100 μm) to a shaped article made from a polymer containing little or no stabilizer of the formula (1) or (1A). Application may be made at the same time as the shaping of the base structure, for example by coextrusion. However, application can also be made to the ready-formed base structure, for example by lamination with a film or by coating with a solution. The outer layer or layers of the finished article have the function of a UV filter, which protects the interior of the article from UV light. The outer layer preferably contains 5-15% by weight, in particular 5-10% by weight, of at least one compound of the formula (1) or (1A).

The polymers stabilized in this way are notable for high weathering resistance, especially for high resistance to UV light. This enables them to retain their mechanical properties and their colour and gloss for a long time even when used outside.

Likewise of particular interest is the use of the novel compounds of the formula (1) or (1A) as stabilizers for coatings, for example for paints. The invention therefore also relates to those compositions whose component (A) is a film-forming binder for coatings.

The novel coating composition preferably comprises 0.01-10 parts by weight of (B), in particular 0.05-10 parts by weight of (B), especially 0.1-5 parts by weight of (B), per 100 parts by weight of solid binder (A).

Multilayer systems are possible here as well, where the concentration of the novel stabilizer (component (B)) in the outer layer can be relatively high, for example from 1 to 15 parts by weight of (B), in particular 3-10 parts by weight of (B), per 100 parts by weight of solid binder (A).

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates.

The binder (component (A)) can in principle be any binder which is customary in industry, for example those described in Ullmann's Encyclopedia of Industrial Chemistry, 5th Edition, Vol. A18, pp. 368-426, VCH, Weinheim 1991. In general, it is a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component (A) can be a cold-curable or hot-curable binder; the addition of a curing catalyst may be advantageous. Suitable catalysts which accelerate curing of the binder are described, for example, in Ullmann's Encyclopedia of Industrial Chemistry, Vol. A18, p. 469, VCH Verlagsgesellschaft, Weinheim 1991.

Preference is given to coating compositions in which component (A) is a binder comprising a functional acrylate resin and a crosslinking agent.

Examples of coating compositions containing specific binders are 1. paints based on cold- or hot-crosslinkable alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking;
4. one-component polyurethane paints based on aliphatic or aromatic urethanes or polyurethanes and hydroxyl group containing acrylate, polyester or polyether resins;
5. one-component polyurethane paints based on aliphatic or aromatic urethaneacrylates or polyurethaneacrylates having free amino groups within the urethane structure and melamine resins or polyether resins, if necessary with curing catalyst;
6. two-component paints based on (poly)ketimines and aliphatic or aromatic isocyanates, isocyanurates or polyisocyanates;
7. two-component paints based on (poly)ketimines and an unsaturated acrylate resin or a polyacetoacetate resin or a methacrylamidoglycolate methyl ester;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and acrylate resins containing anhydride groups, or unsaturated acrylate resins, or aliphatic or aromatic isocyanates, isocyanurates or polyisocyanates;
12. two-component paints based on unsaturated polyacrylates and polymalonates;
13. thermoplastic polyacrylate paints based on thermoplastic acrylate resins or externally crosslinking acrylate resins in combination with etherified melamine resins;
14. paint systems based on siloxane-modified or fluorine-modified acrylate resins.

In addition to components (A) and (B), the coating composition according to the invention preferably comprises as component (C) a light stabilizer of the sterically hindered amine type, the 2-(2-hydroxyphenyl)-1,3,5-triazine and/or 2-hydroxyphenyl-2H-benzotriazole type, for example as mentioned in the above list in sections 2.1, 2.6 and 2.8. Further examples for light stabilizers of the 2-(2-hydroxyphenyl)-1,3,5-triazine type advantageously to be added can be found e.g. in the publications U.S. Pat. No. 4,619,956, EP-A-434608, U.S. Pat. No. 5,198,498, U.S. Pat. No. 5,322,868, U.S. Pat. No. 5,369,140, U.S. Pat. No. 5,298,067, WO-94/18278, EP-A-704437, GB-A-2297091, WO-96/28431. Of special technical interest is the addition of the 2-(2-hydroxyphenyl)-1,3,5-triazines and/or 2-hydroxyphenyl-2H-benzotriazoles, especially the 2-(2-hydroxyphenyl)-1,3,5-triazines.

To achieve maximum light stability, it is of particular interest to add sterically hindered amines as set out in the above-mentioned list under 2.6. The invention therefore also relates to a coating composition which in addition to components (A) and (B) comprises as component (C) a light stabilizer of the sterically hindered amine type.

This stabilizer is preferably a 2,2,6,6-tetraalkylpiperidine derivative containing at least one group of the formula

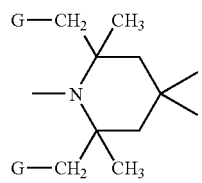

in which G is hydrogen or methyl, especially hydrogen.

Component (C) is preferably used in an amount of 0.05-5 parts by weight per 100 parts by weight of the solid binder.

Examples of tetraalkylpiperidine derivatives which can be used as component (C) are given in EP-A-356 677, pages 3-17, sections a) to f). These sections of this EP-A are regarded as part of the present description. It is particular expedient to employ the following tetraalkylpiperidine derivatives:

bis(2,2,6,6-tetramethylpiperid-4-yl)succinate,
bis(2,2,6,6-tetramethylpiperid-4-yl)sebacate,
bis(1,2,2,6,6-pentamethylpiperid-4-yl)sebacate,
di(1,2,2,6,6-pentamethylpiperid-4-yl)butyl-(3,5-di-tert-butyl-4-hydroxybenzyl)malonate,
bis(1-octyloxy-2,2,6,6-tetramethylpiperid-4-yl)sebacate,
tetra(2,2,6,6-tetramethylpiperid-4-yl)butane-1,2,3,4-tetracarboxylate,
tetra(1,2,2,6,6-pentamethylpiperid-4-yl)butane-1,2,3,4-tetracarboxylate,
2,2,4,4-tetramethyl-7-oxa-3,20-diaza-21-oxo-dispiro[5.1.11.2]heneicosane,
8-acetyl-3-dodecyl-1,3,8-triaza-7,7,9,9-tetramethylspiro[4,5]decane-2,4-dione,
1,1-bis-(1,2,2,6,6-pentamethylpiperidine-4-yl-oxycarbonyl)-2-(4-methoxyphenyl)ethene, or a compound of the formulae

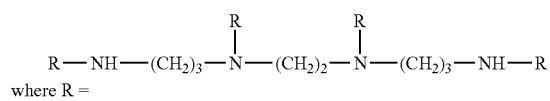
where R =

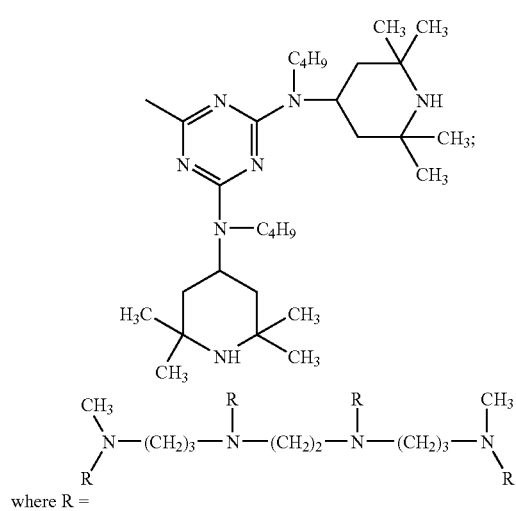

in which m is 5-50.

Apart from components (A), (B) and, if used, (C), the coating composition can also comprise further components, examples being solvents, pigments, dyes, plasticizers, stabilizers, thixotropic agents, drying catalysts and/or levelling agents. Examples of possible components are those described in Ullmann's Encyclopedia of Industrial Chemistry, 5th Edition, Vol. A18, pp. 429-471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride.

Amino-containing resins are simultaneously binder and curing catalyst. Examples thereof are amino-containing acrylate copolymers.

The curing catalyst used can also be a phosphine, for example triphenylphosphine.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the abovementioned publication Ullmann's Encyclopedia of Industrial Chemistry, 5th Edition, Vol. A18, pages 451-453. In radiation-curable coating compositions, the novel stabilizers can also be employed without the addition of sterically hindered amines.

The coating compositions according to the invention can be applied to any desired substrates, for example to metal, wood, plastic or ceramic materials. They are preferably used as topcoat in the finishing of automobiles. If the topcoat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491-500.

Depending on the binder system, the coatings can be cured at room temperature or by heating. The coatings are preferably cured at 50-150° C., and in the case of powder coatings even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formula (1) or (1A) according to the invention. The paint is preferably a topcoat for automobiles. The invention furthermore relates to a process for stabilizing a coating based on organic polymers against damage by light, oxygen and/or heat, which comprises mixing with the coating composition a mixture comprising a compound of the formula (1) or (1A); and to the use of mixtures comprising a compound of the formula (1) or (1A) in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition may be a high-solids paint or can be solvent-free (e.g. a powder coating material). Powder coatings are, for example, those described in Ullmann's Encyclopedia of Industrial Chemistry, 5th Ed., A18, pages 438-444. The powder coating material may also have the form of a powder-slurry (dispersion of the powder preferably in water).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

Preference is also given to the use of the novel compound of the formula (1) or (1A) in photographic materials as stabilizer against damage by light, especially by UV light. The invention therefore also relates to a photographic material comprising a compound of the formula (1) or (1A).

The compounds according to the invention can be used for photosensitive materials of all kinds. For example, they can be employed for colour paper, colour reversal paper, direct-positive colour material, colour negative film, colour positive film, colour reversal film and other materials. They are preferably used, inter alia, for photosensitive colour material which comprises a reversal substrate or which forms positives.

Furthermore, the novel compounds can be combined with other UV absorbers, especially those which are dispersible in aqueous gelatin, for example with hydroxyphenylbenzotriazoles (cf. for example U.S. Pat. No. 4,853,471, U.S. Pat. No. 4,973,702, U.S. Pat. No. 4,921,966 and U.S. Pat. No. 4,973,701), benzophenones, oxanilides, cyanoacrylates, salicylates, acrylonitriles or thiazolines. In this context it is advantageous to employ these further, oil-dissolved UV absorbers in the photographic material in layers other than those comprising the novel UV absorbers.

In particular, it is possible successfully to stabilize photographic materials similar to those described in U.S. Pat. No. 4,518,686.

The invention therefore additionally relates to a photographic material comprising, on support, a blue-sensitive, a green-sensitive and/or a red-sensitive silver-halide emulsion layer and, if desired, a protective layer, with a layer comprising a UV absorber being arranged above the uppermost silver-halide emulsion layer, wherein the UV absorber is a compound of the formula (1) or (1A).

Preference is additionally given to photographic materials which have a layer comprising a compound of the formula (1) or (1A) above the uppermost silver-halide emulsion layer and/or between the green- and red-sensitive silver-halide emulsion layers.

Furthermore, it may be advantageous for all or some of the said layers which can comprise a UV absorber to have a UV absorber mixture and/or a further UV absorber which is dispersible in aqueous gelatin, but a compound of the formula (1) or (1A) must be present at least in one layer.

The novel material preferably has gelatin interlayers between the silver-halide emulsion layers.

Preference is given to photographic materials in which the silver halide in the blue-sensitive, green-sensitive and/or red-sensitive layer is silver chloride bromide comprising at least 90 mol % of silver chloride.

The compounds of the formula (1) or (1A) which are used in accordance with the invention can be incorporated, alone or together with the colour coupler and, if used, further additives, into the colour photographic material by dissolving the compounds beforehand in high-boiling organic solvents. It is preferred to use solvents which boil at higher than 160° C. Typical examples of such solvents are the esters of phthalic acid, phosphoric acid, citric acid, benzoic acid or of fatty acids, and also alkylamides and phenols.

Preferred colour couplers for use in the compositions of the invention, examples of such compounds, further additives such as colour cast inhibitors, DIR couplers and further light stabilizers, such as UV absorbers, phenols, phosphorus(III) compounds, organometallic complexes, hydroquinones and hydroquinone ethers, and more precise details on the structure of various photographic materials, can be found, for example, in the publications EP-A-531 258 and EP-A-520 938, and in the literature cited therein.

The novel triazine compounds of the formula (1) or (1A) are also suitable for use in a process for the photochemical stabilization of undyed, dyed or printed fibre materials comprising for example, silk, leather, wool, polyamide, polyester or polyurethanes, and especially cellulose-containing fibre materials of all kinds. This process forms a further aspect of the present invention. Examples of such fibre materials are the natural cellulose fibres, such as cotton, linen, jute and hemp, and also viscose staple fibre and regenerated cellulose. Preferred textile fibre materials are those of cotton or polyester. The novel triphenyl-substituted triazine compounds are also suitable for the photochemical stabilization of hydroxyl-containing fibres in blend fabrics, for example blends of cotton with polyester fibres or polyamide fibres. A further preferred area of application relates to the blocking or reduction of the UV radiation which passes through the abovementioned textile materials (UV cutting) and the heightened sun protection which textile materials finished with a novel compound offer to the human skin.

As textile fibre material to be treated, polyester- or cellulose acetate-containing fibre materials are of particular interest. Examples of polyester fibres are, e.g., cellulose ester fibres such as cellulose-21/2-acetate fibres and -triacetate fibres, especially linear polyester fibres, optionally those modified with acid. These polyester fibres may be obtained by condensation of terephthalic acid with 1,4-bis(hydroxymethyl)-cyclohexane. Also of interest are fibres from copolymers of terephthalic- and isophthalic acid and ethylene glycol. Conventional polyester fibres in the textile industry are particularly those comprising terephthalic acid and ethylene glycol.

The textile material to be treated may also be a mixed fabric of polyester fibres and other fibres, e.g., polyacrylonitrile/polyester-, polyamide/polyester-, polyester/cotton-, polyester/viscose- or polyester/wool mixed fibres, which may be discontinuously or continuously dyed or printed in conventional manner.

The textile material can be used in various forms, for example as piece goods such as knitted goods or fabrics, or as yarns, e.g. on cheeses or warp beams.

Also very suitable for use in the process of the present invention are textile fabrics which are used in the outerwear garment sector and which are at least partly permeable to light. By the use of such textiles, treated according to the process of the present invention, skin tissue under the outerwear garment can be protected against the damaging effects of UV-radiation. This protective effect is known as UV-cutting and is manifested in that the textile fibre material treated with a compound of formula (1) or (1A) has a significantly increased Ultraviolet Protection Factor (UPF), relative untreated textile fibe material.

The UPF is defined as the quotient of the dose of UV radiation which damages protected skin to that which damages unprotected skin. Accordingly, a UPF is also a measure of the extent to which untreated fibre materials and fibre materials treated with a novel compound of the formula (1) or (1A) are permeable to UV radiation. The determination of the ultraviolet protection factor of textile fibre materials is explained, for example, in WO 94/04515 or in J. Soc. Cosmet. Chem. 40, 127-133 (1989) and can be carried out analogously thereto.

The compound of formula (1) or (1A) is added in an amount of 0.01 to 5% by weight, preferably 0.1 to 3% by weight and, in particular, from 0.25 to 2% by weight, based on the weight of the fibre material.

The compounds of formula (1) or (1A) are only sparingly soluble in water and are therefore applied in dispersed form. The dispersions are formed by grinding the compounds of formula (1) or (1A) in water, using an appropriate dispersing agent, with the aid, e.g., of quartz spheres and a high-speed stirrer, until the particle size required for applicational conditions has been attained.

Examples of dispersing agents for the compounds of formula (1) or (1A) include, e.g.

acid esters or their salts of alkylene oxide adducts, such as acid esters or their salts of a polyadduct of 4 to 40 mol ethylene oxide on 1 mol of a phenol, or phosphoric acid esters of the adducts of 6 to 30 mol ethylene oxide on 1 mol of 4-nonylphenol, on 1 mol of dinonylphenol or, especially, on 1 mol of compounds which are produced by addition of 1 to 3 mol of optionally substituted styrenes on to 1 mol of phenol;

polystyrene sulfonates;

fatty acid taurides;

alkylated diphenyl oxide-mono- or -di-sulfonates;

sulfonates of polycarboxylic acid esters;

addition products, converted into an acid ester with an organic dicarboxylic acid or an inorganic polybasic acid, of 1 to 60, preferably 2 to 30 mol of ethylene oxide and/or propylene oxide, on $C_8$-$C_{22}$-fatty amines, fatty amides, fatty acids or fatty alcohols, or on $C_3$-$C_6$-alcohols having 3-6 hydroxy groups;

lignin sulfonates; and, particularly preferably formaldehyde-condensation products such as condensation products of lignin sulfonates and/or phenol and formaldehyde, condensation products of formaldehyde with aromatic sulfonic acids, such as condensation products of ditolylether sulfonates and formaldehyde, condensation products of naphthalene sulfonic acids and/or naphthol- or naphthylamine-sulfonic acids with formaldehyde, condensation products of phenol sulfonic acids and/or sulfonated dihydroxydiphenylsulfone and phenols or cresols with formaldehyde and/or urea, as well as condensation products of diphenyloxide-disulfonic acid derivatives with formaldehyde.

The textile material to be stabilised is preferably dyed textile material, in particular textile material dyed with dispersion dyes which are only slightly soluble in water. These dyes are therefore present in the dye liquor predominately as a fine dispersion. They may be of various dyes classes such as the acridone-, azo-, anthraquinone-, coumarine-, methine-, perinone-, naphthoquinoneimine-, quinophthalone-, styryl- or nitro-dye classes. Mixtures of dispersion dyes can also be used according to the present invention.

The dyeings are conducted. from aqueous baths using a continuous or discontinuous process. For discontinuous processes (exhaustion processes), the liquor ratio can be selected from within a wide range, e.g. 1:1 to 1:100, preferably 1:6 to 1:50. The dyeing temperature is at least 50° C. and is generally not higher than 140° C. Preferably the dyeing temperature is in the range of from 80 to 135° C.

For continuous processes, the dye baths, which can contain further auxiliaries as well as the dyes, are applied to the piece goods, for example by foularding, spraying or slop padding, and are developed by thermofixing or high temperature steam processes.

Linear polyester fibres and cellulose fibres are preferably dyed by the so-called high temperature processes, in closed and pressure-resistant apparatus, at temperatures above 100° C., preferably between 110 and 135° C. and optionally under pressure. Suitable closed vessels are, e.g., circulation apparatus, such as cheese- or beam dyeing machines, winch vats, jet- or drum dyeing machines, muff-dyeing apparatus, paddles or jiggers.

Cellulose-21/2-acetate fibres are preferably dyed at temperatures of 80-85° C.

If the compounds of formula (1) or (1A) are added during the dyeing application, they may be so applied that the fibre material is first treated with them and the dyeing is then conducted or, preferably, the fibre material is treated simultaneously with the compounds of formula (1) or (1A) and the dyestuff in the dyebath. The application of the compounds of formula (1) or (1A) can also be effected, however, subsequently on the finished dyeing by means of thermofixing, e.g. at 190 to 230° C. over a period of 30 seconds to 5 minutes. A pretreatment with the compounds of formula (1) or (1A) is also possible, whereby the textile material is simultaneously surface-fixed.

The dye liquors can also contain further additives such as dyeing auxiliaries, dispersing agents, carriers, wool protection- and wetting agents, as well as de-foamers.

Moreover, the dye baths can contain mineral acids such as sulfuric acid or phosphoric acid, or expediently organic acids such as aliphatic carboxylic acids, e.g. formic acid, acetic acid, oxalic acid or citric acid and/or salts such as ammonium acetate, ammonium sulfate or sodium acetate. The acids are used particularly for the adjustment of the pH-value of the dye bath used, the pH-value lying preferably between 4 and 5.

Preferably, the fibre material is placed initially for 5 minutes at 40 to 80° C. in the bath which contains the dye, the stabiliser compounds of formula (1) or (1A) and optionally further additives, and which is adjusted to a pH-value of 4.5 to 5.5, the temperature is increased to 125 to 130° C. over 10 to 20 minutes, and is further treated at this temperature for 15 to 90 minutes, preferably for 30 minutes.

The finishing of the dyeings is effected by cooling the dye liquor to 50 to 80° C., by rinsing the dyeings with water and optionally by cleaning in conventional manner in alkaline medium under reductive conditions. The dyeings are then rinsed again and dried. If vat dyes are used for the cellulose component, the goods are first treated with hydrosulfite at a pH-value of 6 to 12.5, in conventional manner, then treated with an oxidising agent and finally washed out.

For the production of prints, the stabiliser compounds of formula (1) or (1A), in the form of their aqueous dispersions, are mixed with the printing pastes. The printing pastes contain e.g. 0.1 to 10%, preferably 0.1 to 5%, of the corresponding stabiliser compounds of formula (1) or (1A), based on the weight of the printing paste.

The amount of the dyestuff which is added to the printing paste depends on the desired colour shade; generally, amounts of 0.01 to 15, preferably 0.02 to 10 weight %, based on the textile material used, suffice.

In addition to the dyestuffs and the aqueous dispersions of the stabiliser compounds of formula (1) or (1A), the printing pastes also conveniently contain acid-stable thickeners, preferably those of natural origin such as carob bean flour derivatives, especially sodium alginate, either used alone or mixed with modified cellulose, especially with preferably 20 to 25 weight % of carboxymethylcellulose. The printing pastes can also contain acid donors such as butyrolactone or sodium hydrogen phosphate, stabilisers, sequestering agents, emulsifiers, water-insoluble solvents, oxidising agents or deaerating agents.

Preferred stabilisers are formaldehye-liberating agents, such as paraformaldehyde or trioxan, especially aqueous solutions containing 30 40-weight % of formaldehyde; sequestering agents are e.g. sodium nitrilotriacetate, sodium ethylenediaminotetraacetate, especially sodium polymetaphosphate, in particular sodium hexametaphosphate; emulsifiers are preferably adducts of an alkylene oxide and a fatty alcohol, especially an adduct of oleyl alcohol and ethylene oxide; water-insoluble solvents are preferably high-boiling, saturated hydrocarbons, especially paraffins having a boiling range of 160 to 210° C. (so-called white spirits); oxidising agents are e.g. aromatic nitro-compounds, preferably aromatic mono- or dinitrocarboxylic acids or -sulfonic acids, which are optionally used as alkylene oxide adducts, especially nitrobenzene sulfonic acids; and deaerating agents are e.g. high-boiling solvents, preferably turpentine oils, higher alcohols, preferably $C_8$-$C_{10}$-alcohols, terpene alcohols or deaerating agents based on mineral- and/or silicone oils, especially commercial formulations of about 15 to 25 weight % of a mineral- and silicone oil mixture and about 75 to 85 weight % of a $C_8$-$C_{10}$-alcohol, such as 2-ethyl-n-hexanol.

For the printing of the fibre material, the printing paste may be applied directly to the whole or part of the surface, conveniently using printing machines of conventional construction, typically ink-jet printing-, Vigoureux printing-, rotogravure printing-, rotary screen printing and surface screen printing machines.

After the printing, the fibre material may be dried at temperatures up to 150° C., preferably at 80 to 120° C.

The subsequent fixation of the fibre material is usually effected by a heat treatment at temperatures of preferably 100 to 220° C. The heat treatment is generally conducted using superheated steam under pressure. Depending on the temperature, the fixation may need from 20 seconds to 10 minutes, preferably 4 to 8 minutes.

The prints are finished in conventional manner by rinsing with water, followed by an optional additional cleaning in alkaline medium under reductive conditions, e.g. using sodium dithionite. In the latter case, the print dyeings are again rinsed, de-watered and dried.

The textile fibres treated with the stabiliser compounds of formula (1) or (1A) have good resistance to the damaging effects of light, oxygen and heat. In particular, the stabilisation process according to the present invention enables to provision of polyester dyeings and prints which exhibit high lightfastness and high resistance to sublimation. No specific pre- or after-treatment of the fibre material is necessary with the stabilisation process according to the present invention.

The UV absorbers according to the invention are suitable, furthermore, as photoprotective agents in cosmetic preparations.

The invention additionally relates, therefore, to a cosmetic preparation comprising at least one compound of the formula (1) or (1A) and cosmetically acceptable carriers or auxiliaries.

The novel cosmetic composition contains from 0.1 to 15% by weight, preferably from 0.5 to 10% by weight, based on the overall weight of the composition, of a UV absorber of the formula (1) or (1A) and a cosmetically acceptable auxiliary.

The cosmetic composition can be prepared by physically mixing the novel UV absorber with the auxiliary by means of customary methods, for example by simply stirring together the two materials. Preferably, however, the sparingly water-soluble or water-insoluble UV absorber of the formula (1) or (1A) is ground to a mean particle size of 100-400 nm or less, for example by wet-grinding in water using a suitable grinding aid and with the addition of conventional auxiliary such as a surfactant or a polymer or a mixture thereof. the nanopigment so obtained is incorporated into a conventional sun protection formulation. The production of oil-in-water or water-in-oil emulsions containing one or more pigments and in the presence of one or more oil- or water-soluble UV absorber of the formula (1) or (1A) may be conducted using known methods for the preparation of sun protection emulsions.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, solid stick or as an aerosol formulation.

As a water-in-oil or oil-in-water emulsion, the cosmetically acceptable auxiliary preferably contains from 5 to 50% of an oily phase, from 5 to 20% of an emulsifier and from 30 to 90% water. The oil phase mentioned can comprise any oil which is suitable for cosmetic formulations, for example one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For the cosmetic formulations according to the invention it is possible to use any conventionally employed emulsifier, for example one or more ethoxylated esters of naturally occurring derivatives, for example polyethoxylated esters of hydrogenated castor oil; or a silicone oil emulsifier such as silicone polyol; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also comprise further components, for example emollients, emulsion stabilizers, skin moisteners, tanning accelerators, thickeners such as xanthan, moisture retention agents such as glycerol, preservatives, or fragrances and colourants.

The novel cosmetic formulations are notable for good protection of human skin and/or hair against the damaging effect of sunlight while at the same time providing for reliable tanning of the skin.

The following Examples further illustrate the present invention.

EXAMPLE 1

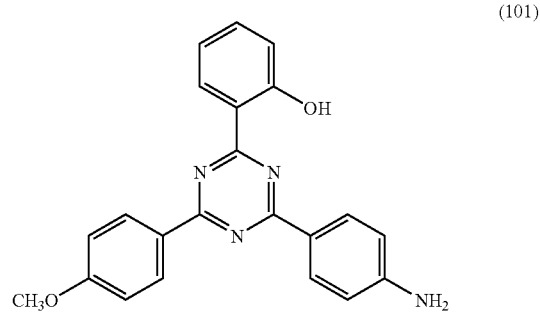

(101)

30 g of 4-methoxybenzoyl chloride are stirred with 12 g of salicylamide for 30 minutes at 170° C. A homogeneous oil is produced which crystallises on cooling. The resulting crystalline mass is treated with a suspension of 18.7 g of p-aminobenzamidine:2 HCl in 500 mls of methanol and with 40 g of a 30% aqueous sodium methylate solution. The mixture so obtained is boiled under reflux for an hour. After the resulting mixture is cooled and filtered, there are obtained 25.8 g (79.5% theory) of a light-yellow product having a melting point of 281-283° C. The UV spectra reading [$\lambda_{max}$(nm)/$\epsilon$(L/mol.cm)] is 335/44195, as determined in $CHCl_3$ at 25° C.

Elemental analysis of the compound having the formula (101) and having the empirical formula $C_{22}H_{18}N_4O_2$ gives:

Req. % C, 71.37; H, 4.9; N, 15.13; O, 8.64.

Found % C, 71.27; H, 4.99; N, 15.7; O, 8.97.

EXAMPLE 2

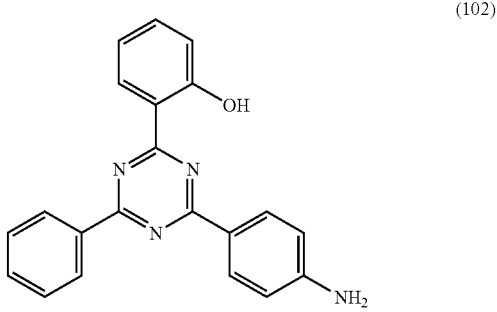

(102)

The procedure described in Example 1 is repeated except that 4-methoxybenzoyl chloride is replaced by the equivalent amount of benzoyl chloride. After working up, the compound of formula (102) is obtained in a yield of 81% of theory and has a melting point of 293-294° C. The UV spectra readings [$\lambda_{max}$(nm)/$\epsilon$(L/mol.cm)] are 275/33035 and 348/34825, as determined in $CHCl_3$ at 25° C.

Elemental analysis of the compound having the formula (102) and having the empirical formula $C_{21}H_{16}N_4O$ gives:

Req. % C, 74.1; H, 4.74; N, 16.46; O, 4.7.
Found % C, 74.0; H, 4.8; N, 16.4; O, 4.8.

EXAMPLE 3

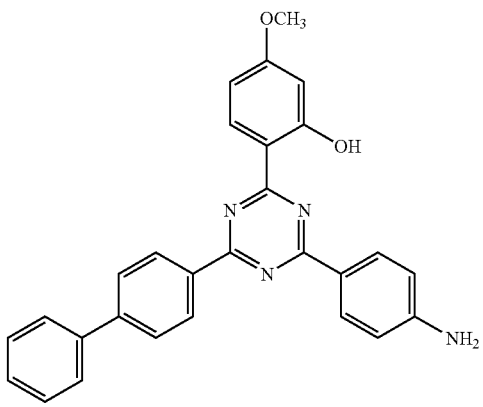
(103)

The procedure described in Example 1 is repeated except that 4-methoxybenzoyl chloride is replaced by the equivalent amount of biphenyl-4-carboxylic acid chloride and salicylamide is replaced by the equivalent amount of 4-methoxy salicylamide. After working up, the compound of formula (103) is obtained in a yield of 66% of theory and has a melting point of 244-247° C. The UV spectra reading [$\lambda_{max}$(nm)/$\epsilon$(L/mol.cm)] is 334/58810, as determined in CHCl$_3$ at 25° C.

Elemental analysis of the compound having the formula (103) and having the empirical formula $C_{28}H_{22}N_4O_2$ gives:

Req. % C, 75.32; H, 4.97; N, 12.55; O, 7.17.
Found % C, 74.97; H, 5.05; N, 12.39; O, 7.62.

EXAMPLE 4

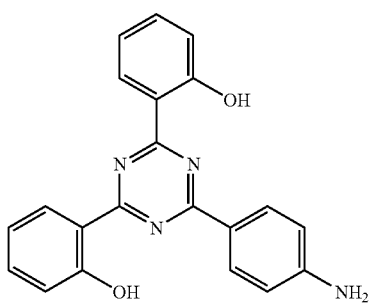
(104)

The procedure described in Example 1 is repeated except that 4-methoxybenzoyl chloride is replaced by the equivalent amount of salicylic acid chloride. After working up, the compound of formula (104) is obtained in a yield of 91% of theory and has a melting point of 327-328° C.

Elemental analysis of the compound having the formula (104) and having the empirical formula $C_{21}H_{16}N_4O_2$ gives:

Req. % C, 70.78; H, 4.53; N, 15.72; O, 8.98.
Found % C, 70.67; H, 4.58; N, 15.72; O, 9.0.

EXAMPLE 5

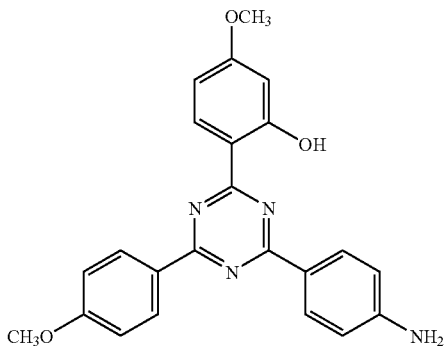
(105)

The procedure described in Example 1 is repeated except that salicylamide is replaced by the equivalent amount of 4-methoxysalicylamide. After working up, the compound of formula (105) is obtained in a yield of 69% of theory and has a melting point of 223-227° C.

Elemental analysis of the compound having the formula (105) and having the empirical formula $C_{23}H_{20}N_4O_3$ gives:

Req. % C, 68.99; H, 5.03; N, 13.99; O, 11.99.
Found % C, 69.06; H, 5.08; N, 14.02; O, 11.84.

EXAMPLE 6

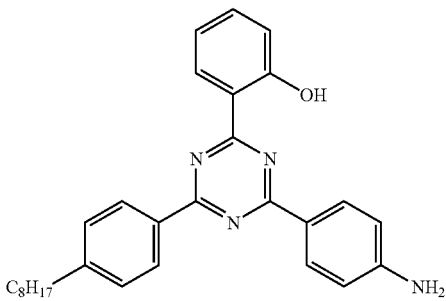
(106)

The procedure described in Example 1 is repeated except that 4-methoxybenzoyl chloride is replaced by the equivalent amount of 4-octylbenzoyl chloride. After working up, the compound of formula (106) is obtained in a yield of 69.5% of theory and has a melting point of 184-185° C.

Elemental analysis of the compound having the formula (106) and having the empirical formula $C_{29}H_{32}N_4O$ gives:

Req. % C, 76.96; H, 7.13; N, 12.38; O, 3.54.
Found % C, 76.97; H, 7.11; N, 12.39; O, 3.53.

EXAMPLE 7

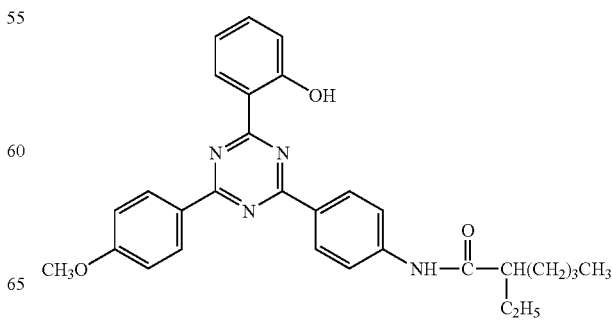
(107)

1 g of the compound of formula (101) in 15 mls of carbon tetrachloride is boiled under reflux for 30 minutes with 0.4 g of pyridine and 0.81 g of 2-ethylhexanoyl chloride. After filtering off the reaction mixture, there are obtained 1.08 g of a light beige crystalline product of formula (107) in a yield of 73% of theory and having melting point of 221-223° C.

Elemental analysis of the compound having the formula (107) and having the empirical formula $C_{30}H_{32}N_4O_3$ gives:

Req. % C, 72.27; H, 6.51; N, 11.24; O, 9.98. 0.4% $H_2O$.
Found % C, 72.49; H, 6.31; N, 11.63; O, 9.57. 0.4% $H_2O$.

EXAMPLE 8

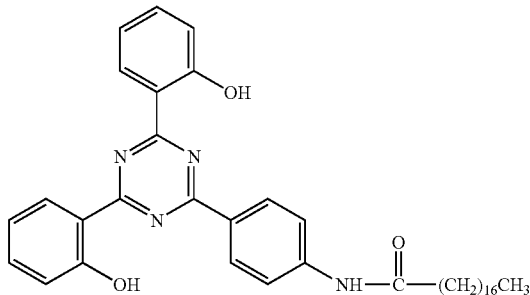

(108)

The procedure described in Example 7 is repeated except that the compound of formula (101) is replaced by the equivalent amount of the compound of formula (107) and 2-ethylhexanoyl chloride is replaced by the equivalent amount of stearoyl chloride. After working up, the compound of formula (108) is obtained in a yield of 98% of theory and has melting point of 222-224° C.

Elemental analysis of the compound having the formula (107) and having the empirical formula $C_{39}H_{50}N_4O_3$ gives:

Req. % C, 75.21; H, 8.09; N, 9.00; O, 7.71.
Found % C, 75.14; H, 8.07; N, 9.02; O, 7.86.

EXAMPLE 9

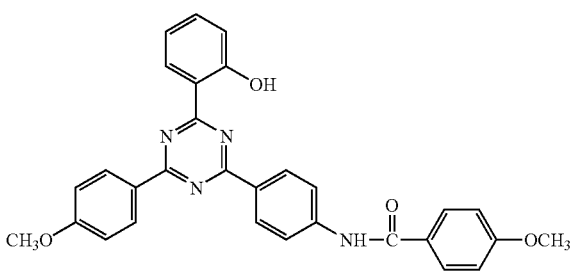

(109)

The procedure described in Example 7 is repeated except that 2-ethylhexanoyl chloride is replaced by the equivalent amount of 4-methoxybenzoyl chloride. After working up, the compound of formula (109) is obtained in a yield of 25% of theory and has melting point of 285-286° C.

Elemental analysis of the compound having the formula (109) and having the empirical formula $C_{30}H_{24}N_4O_4$ gives:

Req. % C, 71.42; H, 4.79; N, 11.10; O, 12.68.
Found % C, 71.25; H, 4.80; N, 11.20; O, 12.75.

EXAMPLE 10

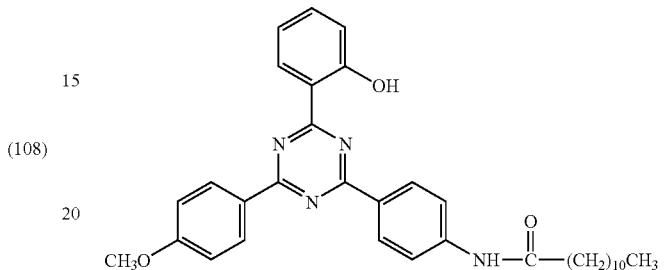

(110)

The procedure described in Example 7 is repeated except that 2-ethylhexanoyl chloride is replaced by the equivalent amount of dodecanoyl chloride. After working up, the compound of formula (110) is obtained in a yield of 92% of theory and has melting point of 182-183° C. The UV spectra reading $[\lambda_{max}(nm)/\epsilon(L/mol.cm)]$ is 320/55035, as determined in $CHCl_3$ at 25° C.

Elemental analysis of the compound having the formula (110) and having the empirical formula $C_{34}H_{40}N_4O_3$ gives:

Req. % C, 73.88; H, 7.29; N, 10.14; O, 8.68.
Found % C, 73.75; H, 7.23; N, 10.09; O, 8.92.

EXAMPLE 11

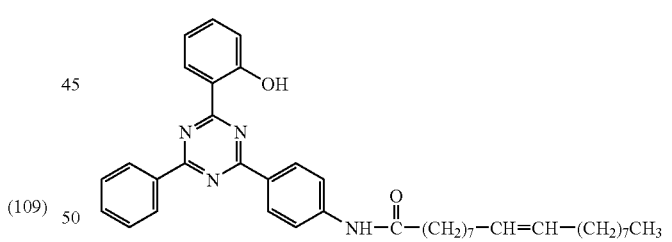

(111)

The procedure described in Example 7 is repeated except that the compound of formula (101) is replaced by the equivalent amount of the compound of formula (102) and that 2-ethylhexanoyl chloride is replaced by the equivalent amount of oleic acid chloride. After working up, the compound of formula (111) is obtained in a yield of 30% of theory and has melting point of 172-173° C. The UV spectra readings $[\lambda_{max}(nm)/\epsilon(L/mol.cm)]$ are 279/38515 and 320/35055, as determined in $CHCl_3$ at 25° C.

Elemental analysis of the compound having the formula (111) and having the empirical formula $C_{39}H_{48}N_4O_2$ gives:

Req. % C, 77.45; H, 8.00; N, 9.26; O, 5.29.
Found % C, 77.14; H, 7.75; N, 9.42; O, 5.69.

EXAMPLE 12

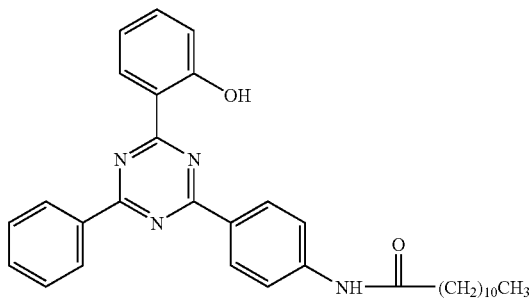
(112)

The procedure described in Example 11 is repeated except that oleic acid chloride is replaced by the equivalent amount of dodecanoyl chloride. After working up, the compound of formula (112) is obtained in a yield of 63% of theory and has melting point of 222-223° C. The UV spectra readings [$\lambda_{max}$ (nm)/$\epsilon$(L/mol.cm)] are 279/37865 and 320/34635, as determined in CHCl$_3$ at 25° C.

Elemental analysis of the compound having the formula (112) and having the empirical formula $C_{33}H_{38}N_4O_2$ gives:
Req. % C, 75.83; H, 7.33; N, 10.72; O, 6.12.
Found % C, 75.7; H, 7.3; N, 10.7; O, 6.3.

EXAMPLE 13

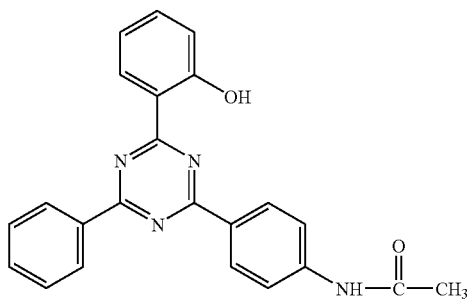
(113)

The procedure described in Example 11 is repeated except that oleic acid chloride is replaced by the equivalent amount of acetyl chloride. After working up, the compound of formula (113) is obtained in a yield of 93% of theory and has melting point of 317-318° C. The UV spectra readings [$\lambda_{max}$ (nm)/$\epsilon$(L/mol.cm)] are 279/37442 and 318/33136, as determined in CHCl$_3$ at 25° C.

Elemental analysis of the compound having the formula (113) and having the empirical formula $C_{23}H_{18}N_4O_2$ gives:
Req. % C, 72.24; H, 4.74; N, 14.65; O, 8.37.
Found % C, 72.0; H, 4.9; N, 14.7; O, 8.4.

EXAMPLE 14

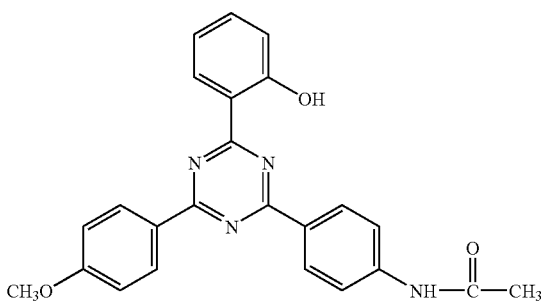
(114)

The procedure described in Example 7 is repeated except that 2-ethylhexanoyl chloride is replaced by the equivalent amount of acetyl chloride. After working up, the compound of formula (114) is obtained in a yield of 99% of theory and has melting point above 300° C. The UV spectra reading [$\lambda_{max}$ (nm)/$\epsilon$(L/mol.cm)] is 321/54075, as determined in CHCl$_3$ at 25° C.

Elemental analysis of the compound having the formula (114) and having the empirical formula $C_{24}H_{20}N_4O_3$ gives:
Req. % C, 69.89; H, 4.89; N, 13.58; O, 11.64.
Found % C, 69.54; H, 4.86; N, 13.52; O, 12.08.

EXAMPLE 15

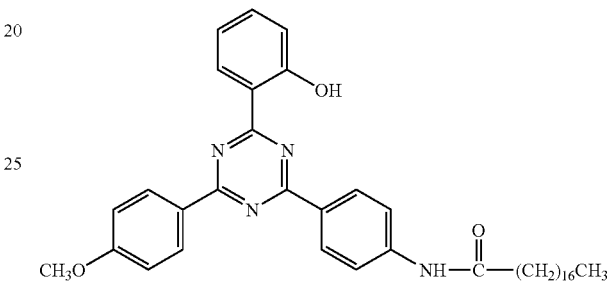
(115)

The procedure described in Example 7 is repeated except that 2-ethylhexanoyl chloride is replaced by the equivalent amount of stearoyl chloride. After working up, the compound of formula (115) is obtained in a yield of 97% of theory and has melting point of 172-173° C.

Elemental analysis of the compound having the formula (115) and having the empirical formula $C_{40}H_{52}N_4O_3$ gives:
Req. % C, 75.44; H, 8.23; N, 8.80; O, 7.54.
Found % C, 75.29; H, 8.04; N, 8.90; O, 7.77.

EXAMPLE 16

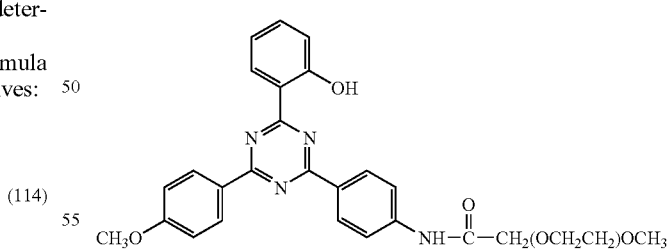
(116)

The procedure described in Example 7 is repeated except that 2-ethylhexanoyl chloride is replaced by the equivalent amount of 3,6,9-trioxadecanoyl chloride. After working up, the compound of formula (116) is obtained in a yield of 65% of theory and has melting point of 125-126° C.

Elemental analysis of the compound having the formula (116) and having the empirical formula $C_{29}H_{30}N_4O_6$ gives:
Req. % C, 65.65; H, 5.70; N, 10.56; O, 18.09.
Found % C, 65.40; H, 5.76; N, 10.39; O, 18.45.

EXAMPLE 17

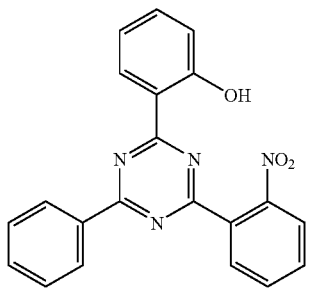
(117A)

A) 4.4 g of salicylamide in 25 mls of xylene (isomeric mixture) are stirred with 12.2 g of 2-nitrobenzoyl chloride for 6 hours at 100° C., until the development of HCl had largely subsided. After cooling, a precipitate forms. The precipitate is separated by suction, washed with xylene and dried to give 10.3 g of colourless crystals. The colourless crystals are then reacted with benzamidine, in methanol at 70° C., to give the compound (117A) as light yellow crystals of m.pt. 181-183° C., in a yield of 80%.

Elemental analysis of the compound having the formula (117A) and having the empirical formula $C_{21}H_{14}N_4O_3$ gives:

Req. % C, 67.1; H, 3.81; N, 15.12.

Found % C, 67.41; H, 3.81; N, 15.10.

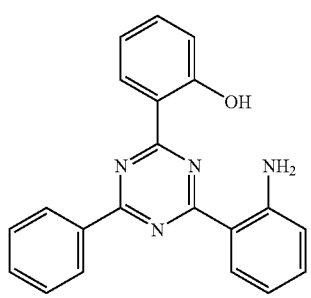
(117)

B) 6.4 g of compound (117A), obtained as described in part A), are hydrogenated in dimethylacetamide using Raney-nickel catalyst. The hydrogenation is conducted at 25° C. at normal pressure over 10 hours. After the catalyst is filtered off, a orange solution remains. Compound (117) is precipitated from the solution by the addition of water. Compound (117) is obtained in an amount of 5.87 g (99% theory) as yellow crystals of m.pt. 218-220° C. The UV spectra readings [$\lambda_{max}$(nm)/ϵ(L/mol.cm)] are 278/45004 and 351/10164, as determined in CHCl$_3$ at 25° C.

Elemental analysis of the compound having the formula (117) and having the empirical formula $C_{21}H_{16}N_4O$ gives:

Req. % C, 74.1; H, 4.74; N, 16.46.

Found % C, 74.11; H, 4.76; N, 16.45.

EXAMPLE 18

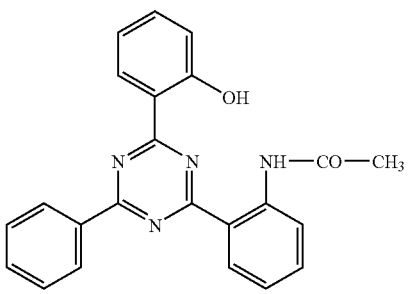
(118)

A solution of 2.28 g of compound (117), obtained as described in Example 17, in dimethylacetamide is reacted with 0.6 g of acetyl chloride at 25° C. and then stirred for 1 hour at 100° C., whereupon a thickly flocculated product is precipitated. After filtration with suction and washing with dimethylacetamide, methanol and petrol, 2.25 g (88%) of the compound of formula (118) are obtained having melting point of 201-203° C. The UV spectra readings [$\lambda_{max}$(nm)/ϵ (L/mol.cm)] are 283/48316 and 354/15277, as determined in CHCl$_3$ at 25° C.

Elemental analysis of the compound having the formula (118) and having the empirical formula $C_{23}H_{18}N_4O_2$ gives:

Req. % C, 72.24; H, 4.74; N, 14.65.

Found % C, 72.60; H, 4.75; N, 14.70.

EXAMPLE 19

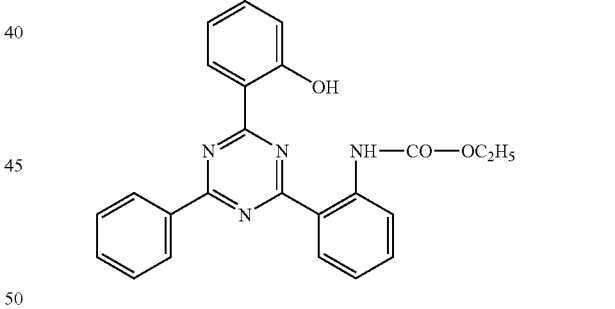
(119)

In an analogous procedure to that described in Example 18, a solution of 2.28 g of the compound (117), obtained as described in Example 17, in dimethylacetamide is reacted with 1.59 g of ethyl chloroformate. After filtration with suction and drying, 1.95 g (69.9%) of the compound of formula (119) are obtained having melting point of 193-195° C. The UV spectra readings [$\lambda_{max}$(nm)/ϵ(L/mol.cm)] are 283/50208 and 355/15368, as determined in CHCl$_3$ at 25° C.

Elemental analysis of the compound having the formula (119) and having the empirical formula $C_{24}H_{20}N_4O_3$ gives:

Req. % C, 69.89; H, 4.88; N, 13.58.

Found % C, 70.12; H, 4.91; N, 13.73.

EXAMPLE 20

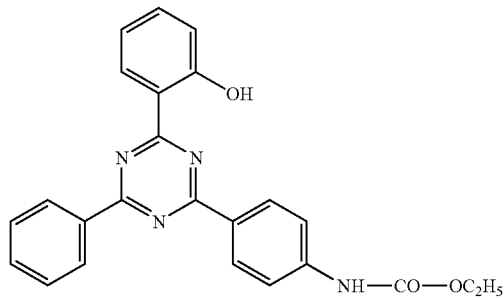
(120)

In an analogous procedure to that described in Example 13, 12.9 g of the compound of formula (102), obtained as described in Example 2, are reacted with ethyl chloroformate. After filtration with suction, washing with carbon tetrachloride and alcohol, and then drying, 14.49 g (93%) of the compound of formula (120) are obtained having m.pt. 247-249° C. The UV spectra readings [$\lambda_{max}$(nm)/$\epsilon$(L/mol.cm)] are 279/37530 and 319/33765, as determined in CHCl$_3$ at 25° C.

Elemental analysis of the compound having the formula (120) and having the empirical formula $C_{24}H_{20}N_4O_3$ gives:
Req. % C, 69.89; H, 4.88; N, 13.58.
Found % C, 69.55; H, 4.88; N, 13.55.

EXAMPLE 21

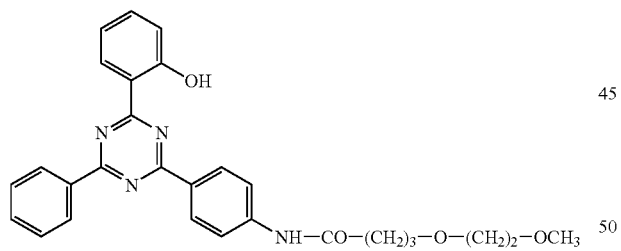
(121)

8.25 g of the compound of formula (120), obtained as described in Example 20, are heated in 10 g of 3-(2-methoxyethoxy)propylamine for 2 hours at 150° C. The reaction mixture is initially clear, it becomes cloudy after 20 minutes and, after 1 hour, it is solid. After cooling, the excess amine is removed by boiling the reaction mixture twice with acetone, using 150 mls of acetone each time. There remains 7.75 g (78%) of almost colourless crystals of the compound (121) having m.pt. 232-234° C. The UV spectra readings [$\lambda_{max}$(nm)/$\epsilon$(L/mol.cm)] are 276/34409 and 342/38834, as determined in CHCl$_3$ at 25° C.

Elemental analysis of the compound having the formula (121) and having the empirical formula $C_{28}H_{29}N_5O_4$ gives:
Req. % C, 67.32; H, 5.85; N, 14.02.
Found % C, 67.42; H, 5.87; N, 14.04.

EXAMPLE 22

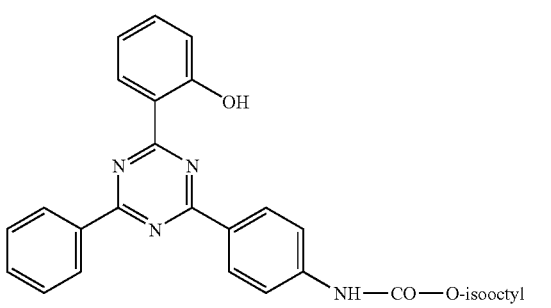
(122)

8 g of the compound of formula (102), obtained as described in Example 2, are suspended in 80 mls of dimethylacetamide and treated with 5.5 g of 2-ethylhexyl chloroformate and the mixture is stirred for 1 hour at 35° C. A clear solution results. The compound (122) is isolated by precipitation in 200 mls of ethyl alcohol. After filtration with suction and washing with ethyl alcohol and petrol ether, there are obtained 10.6 g (90.8%) of light yellow crystals of the compound (122) having m.pt. 172-174° C.

Elemental analysis of the compound having the formula (122) and having the empirical formula $C_{30}H_{32}N_4O_4$ gives:
Req. % C, 72.56; H, 6.49; N, 11.28.
Found % C, 72.55; H, 6.44; N, 11.61.

EXAMPLE 23

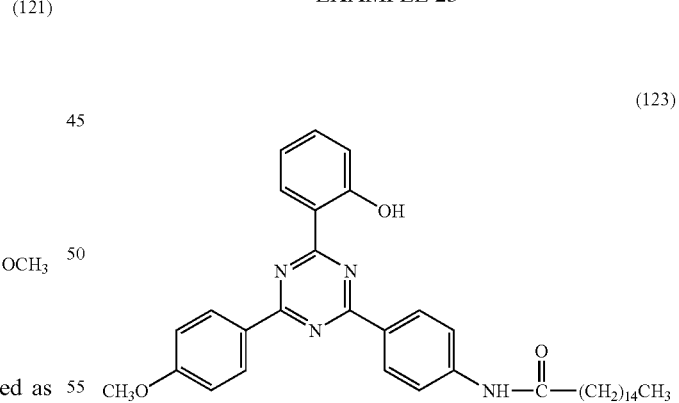
(123)

The procedure described in Example 7 is repeated except that 2-ethylhexanoyl chloride is replaced by the equivalent amount of hexadecanoyl chloride. After working up, the compound of formula (123) is obtained in a yield of 94.5% of theory and has melting point of 165-167° C.

Elemental analysis of the compound having the formula (123) and having the empirical formula $C_{38}H_{48}N_4O_3$ gives:
Req. % C, 75.00; H, 7.95; N, 9.2; O, 7.88.
Found % C, 75.00; H, 7.92; N, 9.1; O, 7.89.

EXAMPLE 24

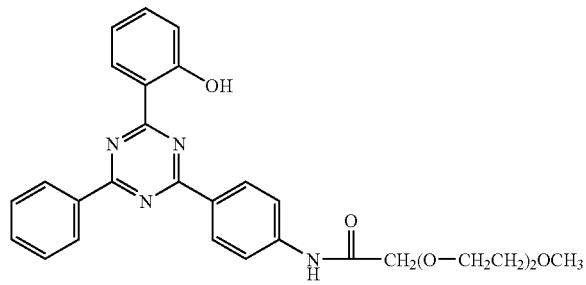

(124)

The procedure described in Example 16 is repeated except that the starting material is the compound of formula (102) instead of the compound of formula (101). After working up, the compound of formula (124) is obtained and has melting point of 90-91° C.

Elemental analysis of the compound having the formula (124) and having the empirical formula $C_{28}H_{28}N_4O_5$ gives:
Req. % C, 67.19; H, 5.56; N, 11.19.
Found % C, 66.80; H, 5.64; N, 11.14.

EXAMPLE 25

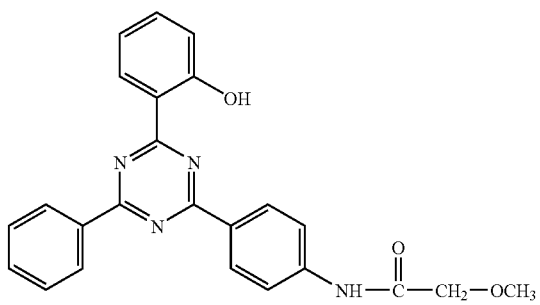

(125)

The procedure described in Example 16 is repeated except that the starting material is the compound of formula (102) instead of the compound of formula (101) and this is reacted with methoxyacetyl chloride. After working up, the compound of formula (125) is obtained in a yield of 89% of theory and has melting point of 213-215° C.

Elemental analysis of the compound having the formula (125) and having the empirical formula $C_{24}H_{20}N_4O_3$ gives:
Req. % C, 69.89; H, 4.89; N, 13.58.
Found % C, 69.96; H, 4.83; N, 13.30.

EXAMPLE 26

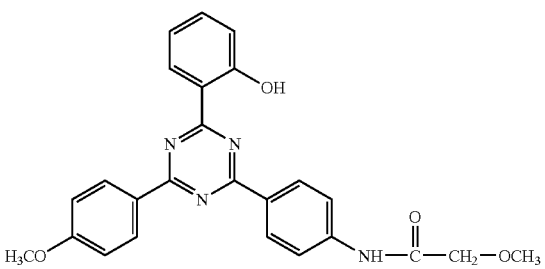

(126)

The procedure described in Example 24 is repeated except that the starting material is the compound of formula (101) instead of the compound of formula (102) and this is reacted with methoxyacetyl chloride. After working up, the compound of formula (126) is obtained in a yield of 89% of theory and has melting point of 195-196° C.

Elemental analysis of the compound having the formula (126) and having the empirical formula $C_{25}H_{22}N_4O_4$ gives:
Req. % C, 67.86; H, 5.01; N, 12.66.
Found % C, 67.33; H, 4.96; N, 12.58.

EXAMPLES 27 TO 32

Determination of Stability to UV Light 100 mg of each test compound is dissolved in 100 mls of chloroform to give a 1000 ppm stock solution. 10 ppm test solutions are prepared by diluting the stock solution twice in the ratio 1/10 with chloroform. Molecular oxygen is removed from the test solution before the irradiation by rinsing for 30 minutes with argon.

200 mls of the test solution so prepared are placed in a UV irradiation apparatus (DEMA 13/2 Fa. Hans Mangels) fitted with a filter system and are irradiated with a UV lamp (HPK-125, Phillips).

The test samples (3 mls each) are withdrawn through a fine PET tube into a 5 ml one-way syringe and subjected directly to UV spectroscopy. A Shimadzu UV-2100 spectometer is used having a recording range of 220-420 nm The determination of photostability is ascertained from the difference between the UV-absorption spectrum of the original compound and that measured after 24 hours exposure to UV irradiation. The measurements are conducted at the wavelength of the absorption maximum, if this lies in the wavelength range 300-400 nm, which is the relevant range for UV stabilisation. If there is no maximum in this range, the absorption difference at 300 nm is measured.

The results are set out in the following Table.

TABLE

| Example | Compound | λ | ε(before) | ε(after) | Δ | % Loss |
|---|---|---|---|---|---|---|
| 27 | 101 | 337 | 1.20 | 0.55 | 0.65 | 54 |
| 28 | 102 | 345 | 1.14 | 0.33 | 0.81 | 71 |
| 29 | 103 | 334 | 1.35 | 0.88 | 0.47 | 35 |
| 30 | 110 | 322 | 1.02 | 0.88 | 0.14 | 14 |
| 31 | 112 | 320 | 0.67 | 0.58 | 0.09 | 13 |
| 32 | 113 | 318 | 0.88 | 0.65 | 0.23 | 26 |

Compounds with poor photostability suffer complete erosion of absorption after exposure for only a few minutes under these test conditions. The results in the Table demonstrate, therefore, the excellent stability of the compounds of the invention when exposed to UV radiation for 24 hours.

EXAMPLE 33

Determination of High-Temperature Lightfastness of Dyed Polyester

A) 5 g of the compound of formula (113) are milled with 2.5 g of a dispersing agent (the condensation product of naphthalene sulfonic acid and formaldehyde) dissolved in 15 mls of water. The milling is conducted in the presence of 25 g of quartz spheres (diameter 1 mm) using a stirrer rotating at 1600 rpm. The milling is continued until the particle size is below 2 microns. The dispersion is separated from the quartz spheres using a fine-mesh screen and the dispersion is adjusted to a content of active substance of 5.5% by the addition of water.

B) A 10 g sample of a polyester tricot is dyed in a high-temperature dyeing apparatus, using a liquor ratio of 1:10. The aqueous dye liquor used contains 2 g/l ammonium sulfate; 0.5 g/l of a dyeing auxiliary (Univadin® 3-flex); 0.5 wt. %, based on the polyester tricot, of the formulation according to step A) above; and 0.83 wt. %, based on the polyester tricot, of a dyestuff mixture containing:

33.7 wt. % of C.I. Disperse Yellow 42,
15.7 wt. % of C.I. Disperse Red 86,
19.3 wt. % of C.I. Disperse Blue 60 and
31.3 wt. % of C.I. Disperse Violet 57.

The dye liquor is adjusted to pH 5 with acetic acid, homogenised and placed in a pressure bomb with the tricot. The dyeing is started at 70° C. and then the temperature is raised to 130° C. over 30 minutes. After a dyeing time of 60 minutes at this temperature, cooling to 75° C. is effected, the dyed goods are rinsed hot and cold and they are reductively cleaned at 70° C. with a liquor containing 3 ml/l of 30% aqueous sodium hydroxide and 2 g/l of sodium dithionite. After rinsing and drying, a grey-dyed polyester tricot is obtained which has a very good high temperature lightfastness.

When the dyeing is conducted using a dye liquor which does not contain the formulation according to step A) above, a dyeing is obtained which has a significantly reduced high temperature lightfastness.

EXAMPLES 34 TO 38

Stabilisation of a 2-Layer Metallic Lacquer

| Various test light stabilisers are dissolved in 20-30 g of an aromatic hydrocarbon mixture (boiling range 182-203° C.) and tested in a clear lacquer having the following composition: | |
| --- | --- |
| acrylate resin (65% solution in xylene/butanol 26:9) | 27.51 |
| acrylate resin (75% solution in an aromatic hydrocarbon mixture (boiling range 161-178° C.) | 23.34 |
| melamine resin (55% solution in isobutanol) | 27.29 |
| butyl acetate/butanol (37:8) | 4.33 |
| isobutanol | 4.87 |
| aromatic hydrocarbon mixture (boiling range 182-203° C.) | 2.72 |
| aliphatic hydrocarbon mixture (boiling range 145-200° C.) | 8.74 |
| flow aid (1% in aromatic hydrocarbon mixture (boiling range 182-203° C.) | 1.20 |
| | 100.00 g |

1.5% by weight of each of the test stabilisers is added to separate samples of the clear lacquer. A further set of test lacquers are prepared which contain, in addition to the test stabilisers of the present invention, 1% by weight of the known light stabiliser compound having the formula:

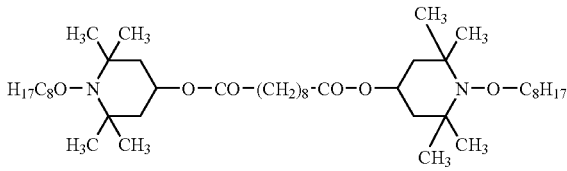

Comparative tests are conducted using clear lacquer samples containing no light stabiliser compounds.

The various clear lacquer samples are diluted with an aromatic hydrocarbon mixture (boiling range 161-178° C.) to obtain a consistency suitable for spraying. The diluted samples are then sprayed on to a prepared aluminium sheet (Uniprime Epoxy, silver metallic base lacquer) and stoved at 130° C. for 30 minutes. A dry film thickness of 40-50 µm of each clear lacquer is obtained.

Each test sample is subjected to weathering using a UVCON® weathering apparatus (UVB-313 lamps) using a cycle consisting of an 8 hour irradiation at 70° C. and a 4 hour condensation at 50° C. The surface gloss of each weathered sample is measured (20° gloss, DIN 67530) initially, and after 400, 800, 1200 and 1600 hours, respectively.

The results obtained using the test light stabilisers of the present invention alone are set out in the following Table:

| | | 20° gloss/exposure hours | | | | |
| --- | --- | --- | --- | --- | --- | --- |
| Example | Test Cpd. | 0 | 400 | 800 | 1200 | 1600 |
| — | none | 92 | 90 | 34 | 15 | — |
| 34 | cpd. (123) | 90 | 84 | 86 | 85 | 74 |
| 35 | cpd. (116) | 92 | 95 | 94 | 94 | 94 |
| 36 | cpd. (115) | 89 | 83 | 82 | 81 | 81 |
| 37 | cpd. (110) | 85 | 67 | 70 | 74 | 66 |
| 38 | cpd. (104) | 92 | 94 | 93 | 92 | 92 |

The results obtained using the test light stabilisers of the present invention together with the known stabiliser are set out in the following Table:

| | | 20° gloss/exposure hours | | | | |
| --- | --- | --- | --- | --- | --- | --- |
| Example | Test Cpd. | 0 | 400 | 800 | 1200 | 1600 |
| — | none | 92 | 86 | 49 | 14 | — |
| 34 | cpd. (123) | 91 | 88 | 87 | 87 | 87 |
| 35 | cpd. (116) | 93 | 94 | 95 | 96 | 96 |
| 36 | cpd. (115) | 90 | 87 | 85 | 82 | 85 |
| 37 | cpd. (110) | 85 | 80 | 74 | 72 | 72 |
| 38 | cpd. (104) | 93 | 94 | 92 | 94 | 94 |

These results clearly demonstrate the improved resistance to weathering (as shown by superior gloss retention) of the stabilised compositions of the invention, relative to the unstabilised compositions.

EXAMPLE 39

Preparation of a Sun Protection Cream

The compound of formula (113) is ground in water containing quartz sand and 8% of phospholipid (Phospholipone 80), as auxiliary, to a mean particle size of 250 nm. The nanopigment suspension so obtained is then incorporated into the following composition.

| Phase A | |
|---|---|
| dimethicone | 2% |
| isopropyl myristate | 9% |
| stearyl alcohol | 10% |
| stearic acid | 4% |
| octyl methoxycinnamate | 3.5% |

| Phase B | |
|---|---|
| triethanolamine | 1.2% |
| Carbomer 934 (1%) | 5.0% |
| compound (113) as 50% suspension | 9.6% |
| | (4.85% active) |
| water | 55.7% |

Phase A is separately very carefully homogenised and, as with Phase B, is then separately heated to 75-80° C. Phase B is then added, with vigorous stirring, to Phase A. Whilst stirring, the mixture is allowed to cool.

Using the SPF analyser (SPF 290 ex Optometrix) the light protection factor of the sun protection cream so obtained is found to be 22. The permeability of the sun protection cream so obtained to the UVA component at 360 nm is zero.

EXAMPLE 40

Preparation of a Sun Protection Emulsion

The compound of formula (102) is ground in water containing "zirconium sand" and 7% of Plantaren 2000 to a mean particle size of 180 nm. The nanopigment suspension so obtained is then incorporated into the following composition.

| Phase A | |
|---|---|
| Ceteareth-6 and stearyl alcohol | 2% |
| Ceteareth-25 | 2% |
| cetearyl alcohol | 5% |
| caprylic/capric triglyceride | 5% |
| cetearyl octanoate | 10% |
| vaseline | 5% |

| Phase B | |
|---|---|
| propylene glycol | 3% |
| Carbopol 934 (1%) | 0.2% |
| compound (113) as 50% suspension | 10% |
| | (5% active) |
| water | 57.53% |

| Phase C | |
|---|---|
| triethanolamine | 0.27% |

Phases A and B are separately heated to 75-80° C. Phase B is then added to Phase A, with vigorous homogenisation, followed by Phase C and the whole is intensively re-homogenised.

Using the SPF analyser (SPF 290 ex Optometrix) the light protection factor of the sun protection cream so obtained is found to be 11. The permeability of the sun protection oil-in-water emulsion so obtained to the UVA component at 360 nm is zero.

EXAMPLES 41 AND 42

10 g of polycarbonate powder (Lexan 115) are dissolved, with stirring at 25° C., in 50 g of methylene chloride. Several hours stirring are required. Then 0.2 g of the test UV absorber is added (2% on the polycarbonate). From the resulting solution there is cast a film having a thickness of 20 microns.

The respective films are exposed in an Atlas Weatherometer CI 65 at a black table temperature of 63° C. and a relative humidity of 60%. At regular intervals, the discolouration of the samples is examined by measuring the Yellowness Index (YI, DIN 6167 method).

In the following Table, there are set out the respective exposure times (in hours) required for the test films to reach a Yellowness Index of 5 or 7.

TABLE

| | | Exposure time (hours) to reach: | |
|---|---|---|---|
| Example | UV absorber | YI = 5 | YI = 7 |
| — | none | 900 | 1000 |
| 41 | compound (125) | 2150 | 3350 |
| 42 | compound (126) | 1780 | 3100 |

Polycarbonate is especially sensitive to light and tends to yellow rapidly. Accordingly, the results in the Table demonstrate that the test compounds used in Examples 41 and 42 are very valuable UV absorbers for polycarbonate.

EXAMPLES 43 AND 44

To 100 parts of polyoxymethylene copolymer (unstabilised) there are added 0.1 part of calcium stearate, 0.1 part of melamine and 0.3 part of an antioxidant (Irganox 245). To this mixture there are then added 0.3 part of a hindered amine light stabiliser (Tinuvin 622) and 0.3 part of the test UV absorber. The powder mixture is mixed well at 25° C. using a "Henkel" mixer. The powder mixture is then extruded to granulate in a double-screw extruder operating at 150 rpm using a temperature profile of 45/180/190° C. The granulate is then converted into plates (2 mm) in an injection moulding device.

The respective plates are exposed in an Atlas Weatherometer CI 65 at a black table temperature of 55° C. using the cycle of 102 minutes dry and 18 minutes wet. At regular intervals, the gloss of the respective plates is determined using a gloss measuring device (Micro Gloss, Byk Gardner) with the adjustment of 60° to the light measurement. The results obtained are set out in the following Table.

TABLE

| Example | UV Absorber | Gloss after 0, 250, 500, 750, 1000 or 1250 hours | | | | | |
|---|---|---|---|---|---|---|---|
| | | 0 | 250 | 500 | 750 | 1000 | 1250 |
| — | none | 78 | 76 | 73 | 73* | 72* | 72* |
| 43 | Cpd. (116) | 79 | 77 | 77 | 78 | 78 | 78 |
| 44 | Cpd. (124) | 76 | 75 | 75 | 75 | 75 | 76 |

*After 750, 1000 and 1250 hours, the control sample developed cracks.

The results demonstrate that the test compounds of Examples 43 and 44 are valuable UV absorbers for use in polyoxymethylene copolymer.

What is claimed is:

1. A cosmetic composition comprising
   (A) at least one organic material which is sensitive to damage by light, oxygen and/or heat, and
   (B) an aqueous nanopigment suspension comprising at least one compound having the formula:

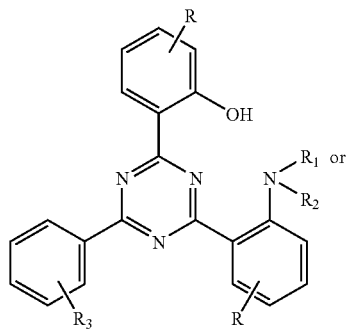

(1)

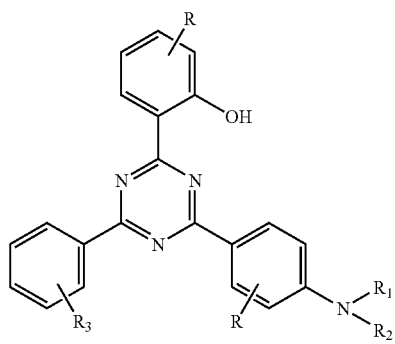

(1A)

wherein
R and $R_1$ are hydrogen;
$R_2$ is —C(=O)—$R_4$ in which $R_4$ is $C_1$-$C_{20}$alkyl, or $C_2$-$C_{20}$alkyl interrupted by 1 to 6 oxygen atoms; and
$R_3$ is hydrogen or $C_1$-$C_{20}$alkoxy,
and a cosmetically acceptable auxiliary,
wherein the compounds of formula (1) or formula (1A) of component (B) have a mean particle size of 100-400 nm; and said composition is present in a cosmetic preparation selected from the group consisting of a water-in-oil emulsion, an oil-in-water emulsion, an oil-in-oil alcohol lotion, a vesicular dispersion of an ionic amphiphilic lipid, a vesicular dispersion of a nonionic amphiphilic lipid, a gel, a solid stick and an aerosol.

2. A composition according to claim 1 wherein component (B) comprises at least one compound having the formula:

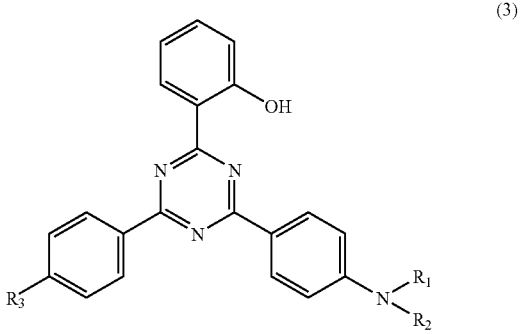

(3)

wherein
$R_1$ is hydrogen;
$R_2$ is —C(=O)—$R_4$ in which $R_4$ is $C_1$-$C_{20}$alkyl or $CH_2$—$(OCH_2CH_2)_n$—$OCH_3$ in which n is an integer from 1 to 5; and
$R_3$ is hydrogen or methoxy.

3. A composition according to claim 2 wherein component (B) comprises at least one compound wherein
$R_2$ is —CO—$CH_3$.

4. A composition according to claim 1 comprising from 0.01 to 15 parts by weight of component (B) per 100 parts by weight of (A).

5. A composition according to claim 1 comprising, in addition to components (A) and (B), one or more further stabilizers or further additives.

6. A composition according to claim 1 comprising, as component (A), a synthetic organic polymer.

7. A process for stabilizing a cosmetic composition against damage by light, oxygen and/or heat, which comprises adding to said preparation a stabilizer of component (B) comprising one or more compounds as described in claim 1.

8. A composition according to claim 1 which is a sunscreen for human skin.

9. A composition according to claim 1 wherein component (B) comprises at least one compound selected from the group consisting of

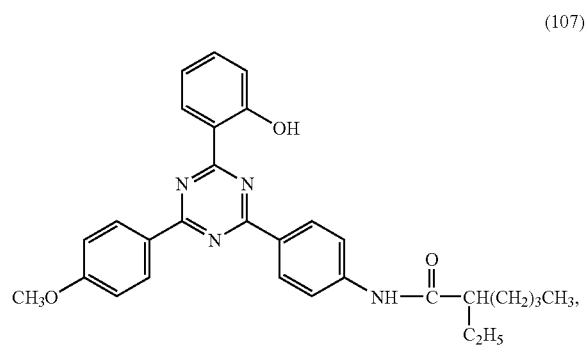

(107)

-continued
(110)
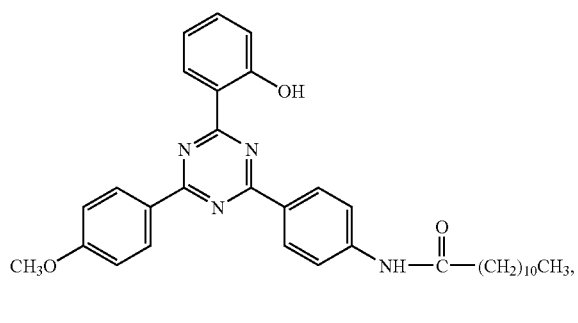
(112)
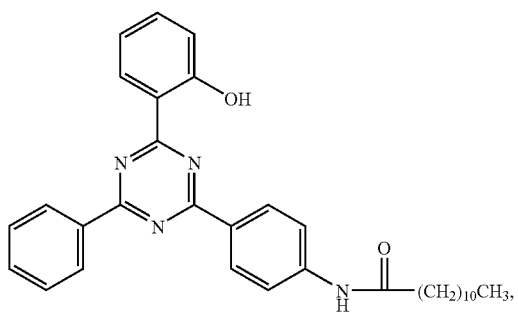
(113)
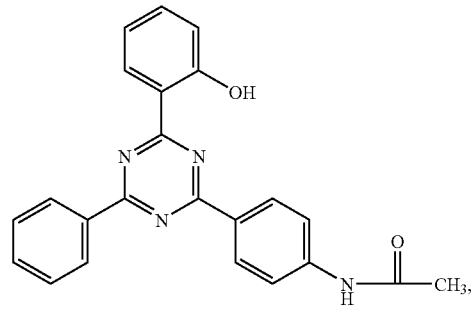
(114)
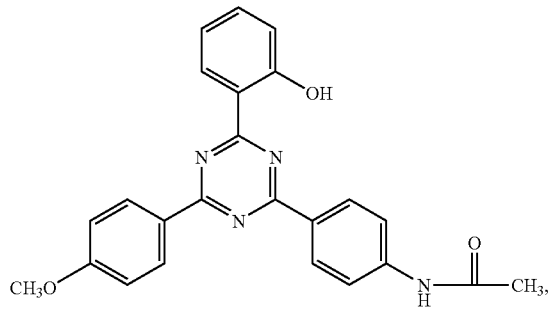
-continued
(115)
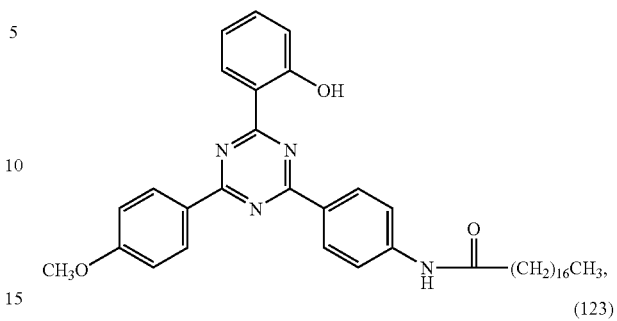
(123)
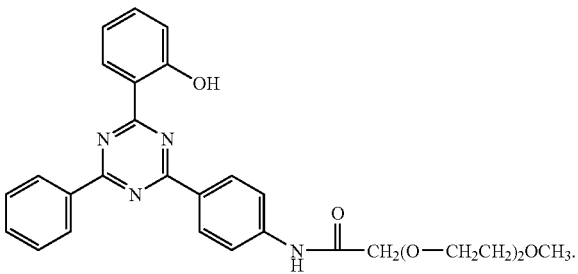
and
(124)
10. A composition according to claim 1 wherein component (B) comprises at least one compound selected from the group consisting of
(116)
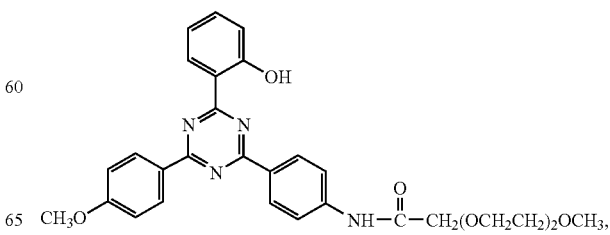

-continued
(121)
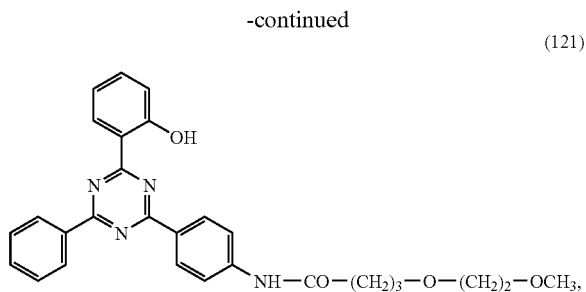
(125)
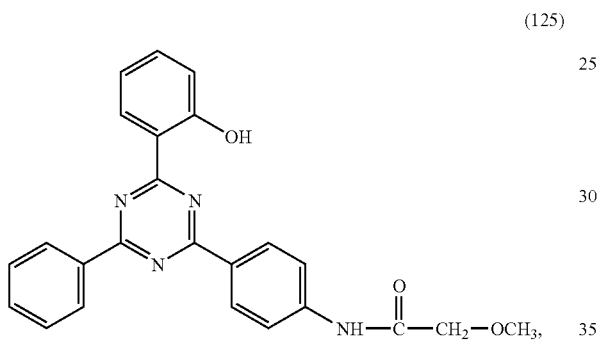
-continued
(126)
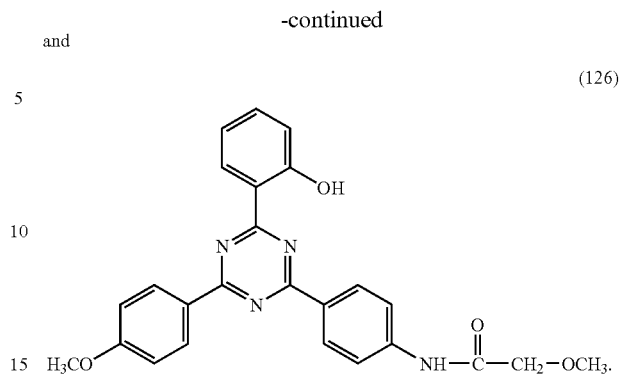
and
11. A composition according to claim 1 wherein component (B) comprises a compound having the formula:
(118)
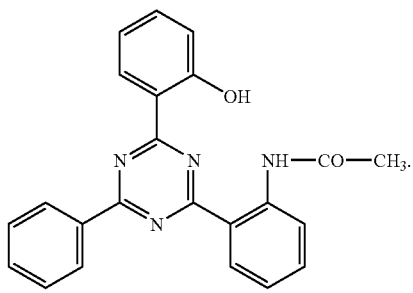
* * * * *